(12) United States Patent
Kashima et al.

(10) Patent No.: US 9,261,437 B2
(45) Date of Patent: Feb. 16, 2016

(54) ATTACHED MATTER INSPECTION DEVICE

(71) Applicant: Hitachi, Ltd., Chiyoda-ku, Tokyo (JP)

(72) Inventors: Hideo Kashima, Tokyo (JP); Masakazu Sugaya, Tokyo (JP); Koichi Terada, Tokyo (JP); Yasutaka Suzuki, Tokyo (JP); Hisashi Nagano, Tokyo (JP); Yasuaki Takada, Tokyo (JP); Yuichiro Hashimoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/422,893

(22) PCT Filed: Jun. 12, 2013

(86) PCT No.: PCT/JP2013/066216
§ 371 (c)(1),
(2) Date: Feb. 20, 2015

(87) PCT Pub. No.: WO2014/045649
PCT Pub. Date: Mar. 27, 2014

(65) Prior Publication Data
US 2015/0233796 A1 Aug. 20, 2015

(30) Foreign Application Priority Data
Sep. 19, 2012 (JP) .................................. 2012-205774

(51) Int. Cl.
*H01J 49/04* (2006.01)
*G01N 31/00* (2006.01)
(Continued)

(52) U.S. Cl.
CPC .......... *G01N 1/2211* (2013.01); *H01J 49/0422* (2013.01); *G01N 2001/028* (2013.01)

(58) Field of Classification Search
USPC ............... 250/281, 292, 288, 441.11, 442.11, 250/526; 73/23.2, 23.3, 23.41, 23.42, 73/28.01, 31.01, 31.07, 863, 863.11, 73/863.02, 863.03, 863.12, 863.23, 73/863.71, 864.33, 432.1
See application file for complete search history.

(56) References Cited

U.S. PATENT DOCUMENTS

| 5,915,268 A * | 6/1999 | Linker ..................... G01N 1/24 422/93 |
| 6,334,365 B1 * | 1/2002 | Linker .................. G01N 1/2214 73/864.71 |

(Continued)

FOREIGN PATENT DOCUMENTS

| JP | 2008-147386 A | 6/2008 |
| JP | 2009-31315 A | 2/2009 |

(Continued)

OTHER PUBLICATIONS

International Search Report (PCT/ISA/210) dated Jul. 9, 2013 with English translation (three pages).

(Continued)

*Primary Examiner* — Bernard E Souw
(74) *Attorney, Agent, or Firm* — Crowell & Moring LLP

(57) ABSTRACT

Sample fine particles attached to an inspection object are identified simply and with high accuracy, and an increase in operation rate and a decrease in device size are achieved. The inspection object is transported into a sampling chamber defined by a pair of side walls and an upper wall enclosing a part of a transport route of a transport unit. The inspection object is sprayed with compressed gas from an air nozzle, the peeled sample fine particles are aspirated into a collector, and the sample fine particles are separated from the aspirated gas for analysis. The air nozzle is disposed on one of the side walls defining the sampling chamber. The collector is disposed under the other side wall as a container independent from the sampling chamber.

12 Claims, 22 Drawing Sheets

(51) Int. Cl.
*G01N 1/22* (2006.01)
*G01N 1/02* (2006.01)

(56) References Cited

U.S. PATENT DOCUMENTS

| | | | | |
|---|---|---|---|---|
| 8,198,092 B2* | 6/2012 | Durack | ............... | C12N 5/0612 422/73 |
| 8,217,339 B2* | 7/2012 | Kashima | ............... | G01N 1/2205 250/281 |
| 8,623,657 B2* | 1/2014 | Durack | ............... | C12N 5/0612 422/73 |
| 2008/0135182 A1* | 6/2008 | Nishikawa | ............... | B08B 5/02 156/536 |
| 2009/0200458 A1* | 8/2009 | Kashima | ............... | G01N 1/2205 250/282 |
| 2013/0171683 A1* | 7/2013 | Durack | ............... | C12N 5/0612 435/29 |
| 2014/0151543 A1 | 6/2014 | Nagano et al. | | |
| 2015/0136975 A1* | 5/2015 | Sugaya | ............... | H01J 49/0422 250/288 |

FOREIGN PATENT DOCUMENTS

| | | |
|---|---|---|
| JP | 2009-31316 A | 2/2009 |
| WO | WO 2006/097990 A1 | 9/2006 |
| WO | WO 2012/063796 A1 | 5/2012 |

OTHER PUBLICATIONS

Japanese-language Written Opinion (PCT/ISA/237) dated Jul. 9, 2013 (three pages).

* cited by examiner

|     | 37a   | 37b   | 37c   |
|-----|-------|-------|-------|
| 32d | Eject | Eject | Eject |
| 32c | Eject | Eject | Eject |
| 32b | Eject | Eject | Eject |
| 32a | Eject | Stop  | Stop  |

|      | 37a   | 37b   | 37c   |
|------|-------|-------|-------|
| 32d  | Stop  | Stop  | Eject |
| 32c  | Stop  | Eject | Eject |
| 32b  | Eject | Eject | Stop  |
| 32a  | Eject | Stop  | Stop  |

FIG. 16

|     | 37a   | 37b   | 37c   |
| --- | ----- | ----- | ----- |
| 32d | Eject | Eject | Eject |
| 32c | Eject | Eject | Eject |
| 32b | Eject | Eject | Stop  |
| 32a | Eject | Stop  | Stop  |

FIG. 17

|     | 37a,28a | 37b,28b | 37c,28c |
| --- | ------- | ------- | ------- |
| 32d | Eject   | Eject   | Eject   |
| 32c | Eject   | Eject   | Eject   |
| 32b | Eject   | Eject   | Stop    |
| 32a | Eject   | Stop    | Stop    |

FIG. 18

|     | 37a   | 37b   | 37c   |
|-----|-------|-------|-------|
| 32d | Stop  | Stop  | Eject |
| 32c | Stop  | Eject | Eject |
| 32b | Eject | Eject | Stop  |
| 32a | Eject | Stop  | Stop  |

ATTACHED MATTER INSPECTION DEVICE

TECHNICAL FIELD

The present invention relates to an attached matter inspection device and an attached matter inspection method for inspecting a substance (sample substance) attached to an inspection object.

BACKGROUND ART

Patent Literatures 1 to 3 disclose technologies for inspecting the presence or absence of attached matter, such as an explosive or narcotic drug, on an inspection object at the boarding gate of an airport or seaport and the like. Patent Literature 4 discloses a technology for preventing the attachment of dust to an object.

In Patent Literatures 1 to 3, it is described that compressed gas is sprayed onto the surface of the inspection object at a wind speed of 20 m/s or more using at least one nozzle, and that the nozzle is moved based on the outer shape of the inspection object by moving joints. It is also described that, using the at least one nozzle for spraying the surface of the inspection object with compressed gas at the wind speed 20 m/s, the compressed gas is also ejected onto an inner wall of a collection unit and/or an arm supporting the nozzle.

The technology proposed by Patent Literature 4 includes a means for ejecting a curtain of air over and along an upper surface a substrate from outside thereof, as the substrate is being transported on a transport belt, and an air suctioning means disposed on the other side, for preventing the attachment of dust and the like onto the substrate using an air flow formed like a curtain over the substrate.

CITATION LIST

Patent Literature

Patent Literature 1: WO2006/097990 A1
Patent Literature 2: JP 2009-031316 A
Patent Literature 3: JP 2009-031315 A
Patent Literature 4: JP 2008-147386 A

SUMMARY OF INVENTION

Technical Problem

In the technologies according to Patent Literatures 1 to 3, a collection filter for collecting sample fine particles is directly connected to a sampling chamber, with the collection filter disposed just below an inspection object delivery unit. It is described that, in order to peel and collect the sample fine particles from the inspection object, the inspection object is bombarded with a jet of air from an air nozzle, and the air in the sampling chamber is aspirated by an aspiration means. In this case, because the wall surfaces of the sampling chamber are continuous in shape to the collection filter, the surface area of the sampling chamber wall surfaces up to the collection filter is large. Thus, there is a high probability that the sample fine particles peeled from the inspection object by the air jet bombardment may become attached to the wall surfaces and deposited thereon. Further, while the interior of the sampling chamber is aspirated by the aspiration means, a large-sized aspiration means is required because of a large volume of the space from just below the inspection object delivery unit to the collection filter. As a result, the attached matter inspection device is increased in size.

The delivery unit is required to drop the sample fine particles peeled from the inspection object into an opening portion just below the delivery unit. Thus, it is necessary to use a delivery means such as a roller having an opening portion in a delivery surface. In this case, there is a high probability of an accident in the delivery process, such as the inspection object being caught or small items falling. When such an accident occurs, the device needs to be stopped, lowering device reliability and operation rate. Further, in order to restore the device, the cause of accident needs to be removed by an attendant trained for device maintenance, which requires labor cost, such as training cost.

The technology according to Patent Literature 4 is aimed at preventing the attachment of dust and the like onto the substrate. Thus, the technology does not involve the direct bombardment of the substrate with air, and therefore cannot peel dust and the like attached to the substrate.

The present invention provides an attached matter inspection device that removes sample fine particles from the surface of the inspection object in a contactless manner, and that inspects whether the sample fine particles include an attached substance.

Solution to Problem

An attached matter inspection device according to the present invention includes a transport unit that transports an inspection object; a sampling chamber defined by a pair of side walls and an upper wall enclosing a part of a transport route of the transport unit; an air nozzle that sprays a gas onto the inspection object transported into the sampling chamber so as to peel sample fine particles attached to the inspection object; a collector that aspirates air in the sampling chamber together with the sample fine particles; and a separation unit that separates the sample fine particles from the aspirated air. The air nozzle is disposed on one of the side walls defining the sampling chamber, and the collector is disposed under the other side wall as a container independent from the sampling chamber.

In the attached matter inspection device according to the present invention, instead of the air nozzle ejecting compressed gas, a fan such as a turbo fan may be used. In this case, the fan may be disposed on one of the side walls defining the sampling chamber, while the collector may be disposed under the other side wall. Preferably, the sampling chamber may include an inner wall having a continuously curved shape for guiding the air blown from the fan to the collector.

By the above configuration, the surface area of the walls constituting the collector may be decreased, whereby the probability of the sample fine particles becoming attached to or deposited on the wall surfaces in the collector can be decreased while the particles are being transported in the collector. Further, the volume of the collector will also be decreased, enabling the use of a small-sized aspiration means and achieving a decrease in the size of the attached matter inspection device. As a result, the area of the surface parallel with the opening portion of the collector can also be decreased, which increases the flow velocity of the air flow in the collector caused by the aspiration by the aspiration means. Thus, the transport speed of the sample fine particles as they are transported by being carried by the air flow in the collector will also be increased, whereby the amount of the sample fine particles becoming attached to or deposited on the wall surfaces forming the collector can also be decreased.

Because the collector need not be disposed just below the delivery unit, a general belt-type delivery means often used in an X-ray transmission inspection device can be used for the delivery unit. Thus, the need for a large opening portion in the lower surface of the delivery unit is eliminated, so that there can be realized an attached matter inspection device that is free of accidents such as the inspection object getting caught or small items dropping into the opening, and that has high reliability and operation rate. The need for a specialized attendant trained in device maintenance is also eliminated, whereby the cost for training or labor can be dispensed with.

When the sampling chamber includes the inner wall having the continuously curved shape connecting to the opening portion of the collector, the sample fine particles transported together with the ejected gas can be introduced into the collector along the curved wall surface. Thus, the sample fine particles can be efficiently introduced into the collector without being scattered to other locations.

By rotating the ejection hole for ejecting the compressed gas perpendicular to the inspection object, a wider surface of the inspection object can be bombarded with the gas, whereby the attached matter inspection of the inspection object can be performed in greater detail.

Advantageous Effects of Invention

According to the present invention, there can be provided a small-sized attached matter inspection device such that the sample fine particles attached to the inspection object can be contactlessly peeled and effectively collected, and the sample fine particles can be inspected simply and with high accuracy.

Other problems, configurations, and effects will become apparent from the following description of embodiments.

BRIEF DESCRIPTION OF DRAWINGS

FIG. 16 is a chart illustrating the relationship between the signal from the inspection object recognition unit and the air nozzles used in first and fourth peeling steps.

FIG. 17 is a chart illustrating the relationship between the signal from the inspection object recognition unit and the air nozzles used in the second peeling step.

FIG. 18 is a chart illustrating the relationship between the signal from the inspection object recognition unit and the air nozzles used in the third peeling step.

DESCRIPTION OF EMBODIMENTS

In the following, modes of carrying out the present invention will be described with reference to the drawings. In the following embodiments, a personal item of a subject to which explosive fine particles or fine particles of an explosive additive may be attached is used as a representative inspection object. The inspection object may also include other objects, such as mail, human body, or an article for import or export to which a substance generally assumed to have an adverse influence on the human body may be attached, such as explosive substance, drugs including stimulant drug, chemical substance having an adverse influence on human body, bacteria, and microbes such as virus.

First Embodiment

Figure 1:
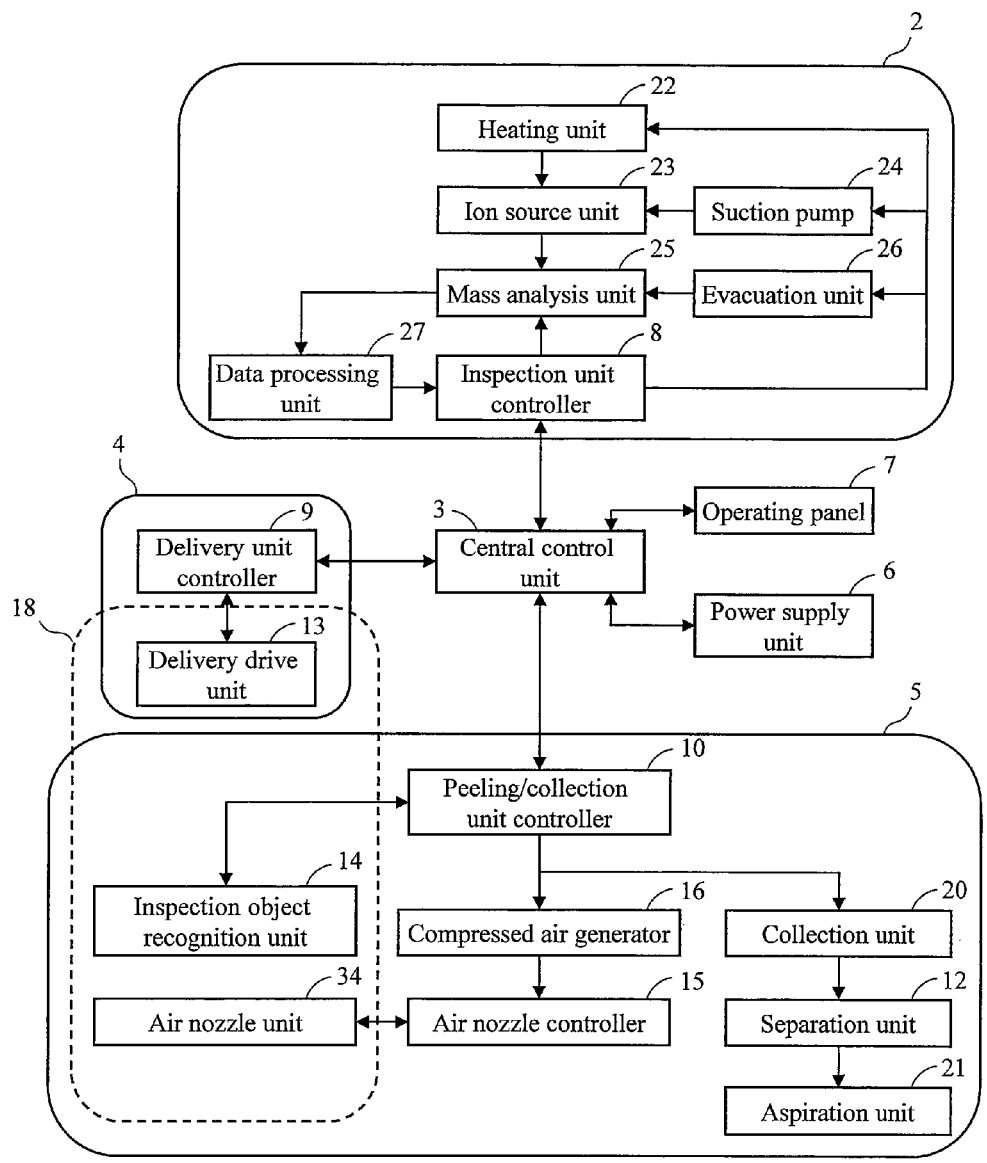
FIG. 1 is a block diagram of main elements of an attached matter inspection device according to the present invention.
Figure 2:
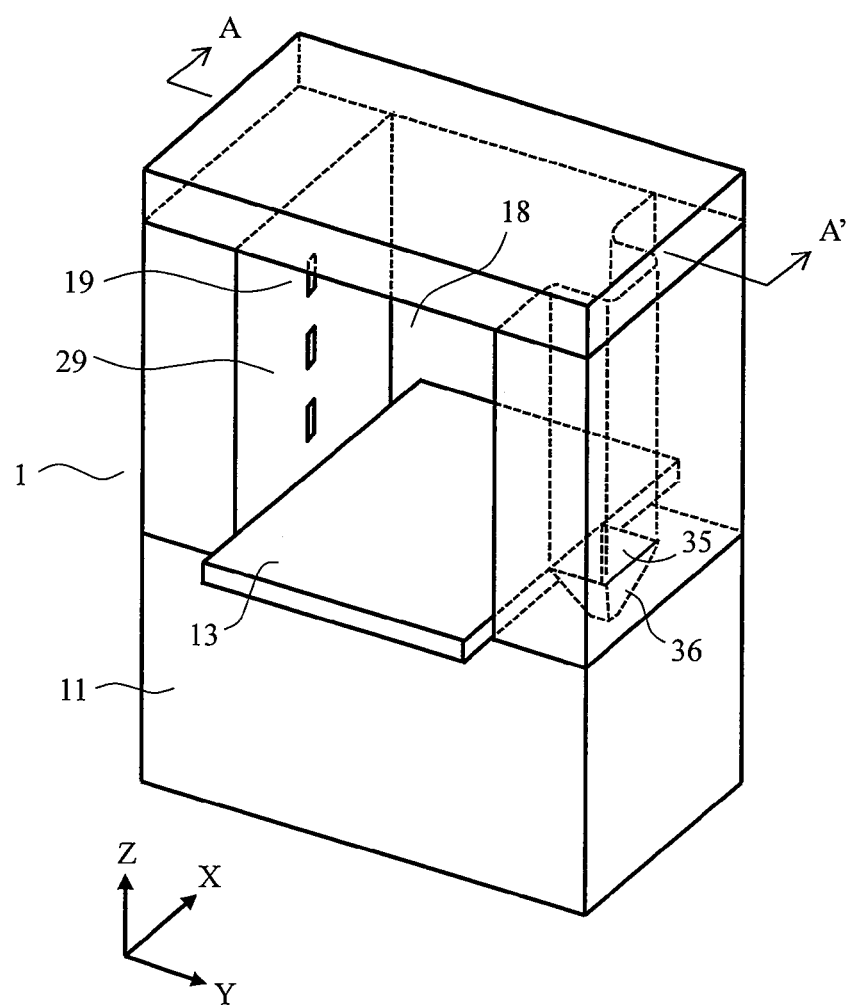
FIG. 2 is a perspective view of an example of the attached matter inspection device according to the present invention.

FIG. 1 is a block diagram of main elements of an attached matter inspection device according to a first embodiment of the present invention. FIG. 2 is a perspective exterior view of the attached matter inspection device according to the first embodiment of the present invention.

The attached matter inspection device 1 according to the present embodiment includes an attached matter inspection unit 2; a central control unit 3; an inspection object delivery (transport) unit 4; a peeling/collection unit 5; a power supply unit 6; and an operation panel 7. The power supply unit 6 supplies electric power required for operation of the various units of the device and is controlled by the central control unit 3. The central control unit 3 is also connected to an inspection unit controller 8, a delivery unit controller 9, and a peeling/collection unit controller 10. Operating conditions for the respective device units are input via the operation panel 7, and the central control unit 3 controls the operation of the various device units in accordance with the input operating conditions.

The attached matter inspection unit 2, the central control unit 3, the inspection object delivery unit 4, the peeling/collection unit 5, and the power supply unit 6 illustrated in FIG. 1 are disposed in an attached matter inspection device housing 11 illustrated in FIG. 2. The operation panel 7 is located at a desired position for easy operation.

The inspection object delivery unit 4 includes a delivery drive unit 13 that transports the inspection object, and the delivery unit controller 9 that controls the delivery drive unit 13. In the peeling/collection unit 5, there are disposed an inspection object recognition unit 14 that recognizes the outer shape of the inspection object; an air nozzle controller 15 that controls an air nozzle unit 34 in accordance with the outer shape of the inspection object detected by the inspection object recognition unit 14; a compressed air generation unit 16 for ejecting compressed air (air jet) via the air nozzle unit 34; a collection unit 20; and an aspiration unit 21 that aspirates the inside of the collector 36 via a separation unit 12 connected to the collection unit 20.

A sampling chamber 18 is defined by a pair of side walls and an upper wall, the chamber enclosing a space above a part of a delivery route for the transport of the inspection object by the drive unit 13. The sampling chamber 18 is provided with the delivery drive unit 13, the inspection object recognition unit 14, and the air nozzle unit 34. The delivery drive unit 13 has a delivery direction parallel with the X-axis in FIG. 2. The air nozzle unit 34 is disposed in a left side wall with respect to the delivery direction of the sampling chamber 18. The collector 36 is disposed in the side wall on the opposite side from the air nozzle unit across the delivery drive unit 13, below a delivery surface of the delivery drive unit 13. The inner surface of the sampling chamber 18 is covered with a smooth cover 19 without any sharp recesses or projections. The side wall of the sampling chamber 18 on the side on which the collector 36 is provided includes a recess portion (groove portion) extending in an upper/lower direction, with the lower end of the recess portion being connected to a collector opening portion 35.

The separation unit 12 in the peeling/collection unit 5 is provided with an insertable/removable collection filter unit for collecting sample fine particles peeled by bombarding the inspection object with air jet, as will be described later. The collection filter unit with the collected sample fine particles is heated to a certain temperature by a heating unit 22 of the attached matter inspection unit 2. The sample fine particles collected by the collection filter unit are heated and vaporized, generating sample gas. The heating unit 22 is connected to an ion source unit 23. The sample gas is introduced into the ion source unit 23 by a suction pump 24 and ionized. The ions generated in the ion source unit 23 are subjected to mass analysis by a mass analysis unit 25. The ion source unit 23 and the mass analysis unit 25 are evacuated by an evacuation unit 26.

The data processing unit 27 includes a storage means in which a database is stored that includes standard mass analysis data (mass-to-charge ratio (mass number of ion/valence of ion) values and relative intensities) required for identifying a plurality of explosive substances. An output signal from a detector in a mass spectrometer of the mass analysis unit 25 is sent to a data processing unit 27 to perform data processing, such as comparing the database read from the storage means with the result of mass analysis of ions derived from an explosive component, so as to identify an explosive substance. The identified explosive substance and/or the mass analysis result are displayed on the operation panel 7.

Figure 3:
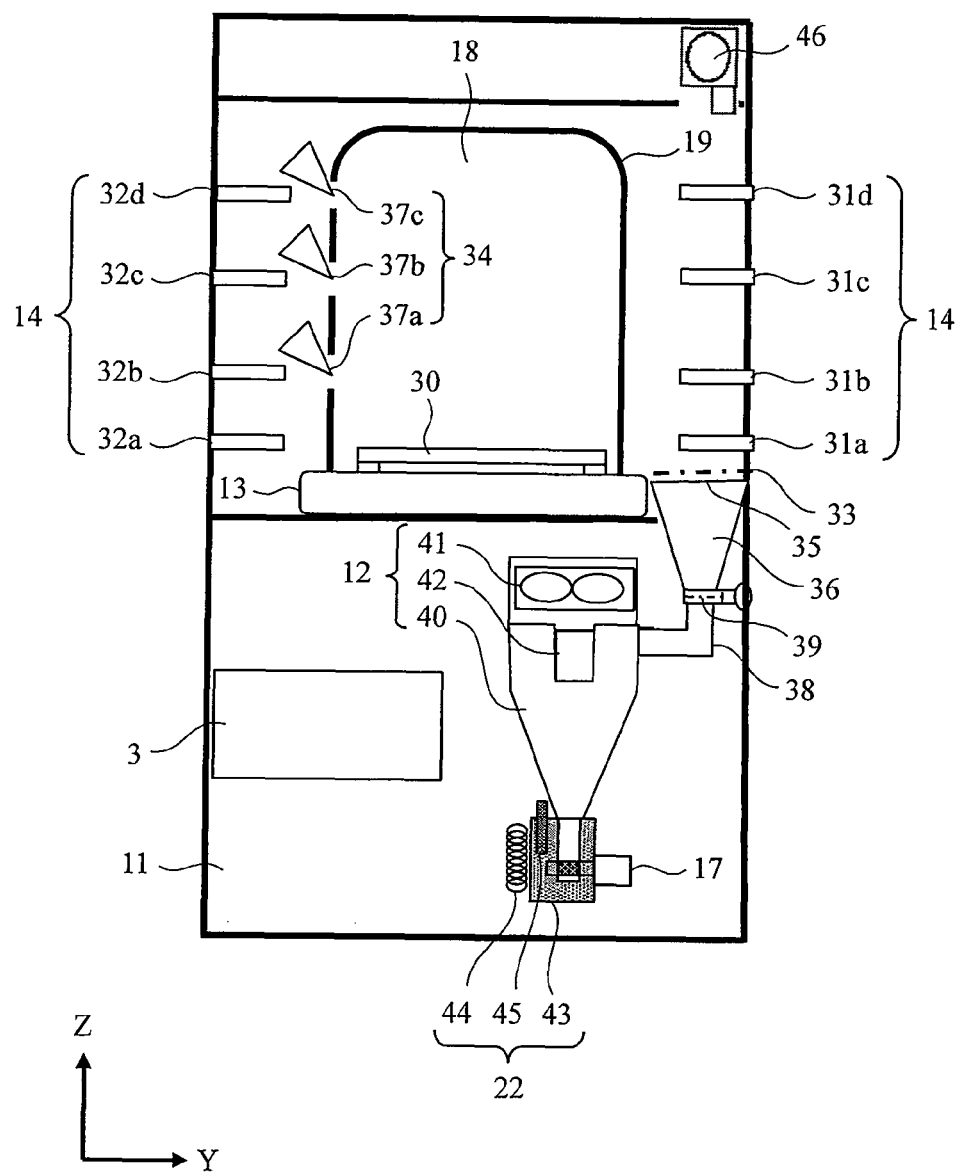
FIG. 3 is a schematic cross sectional view of an example of a peeling/collection unit.
Figure 4:
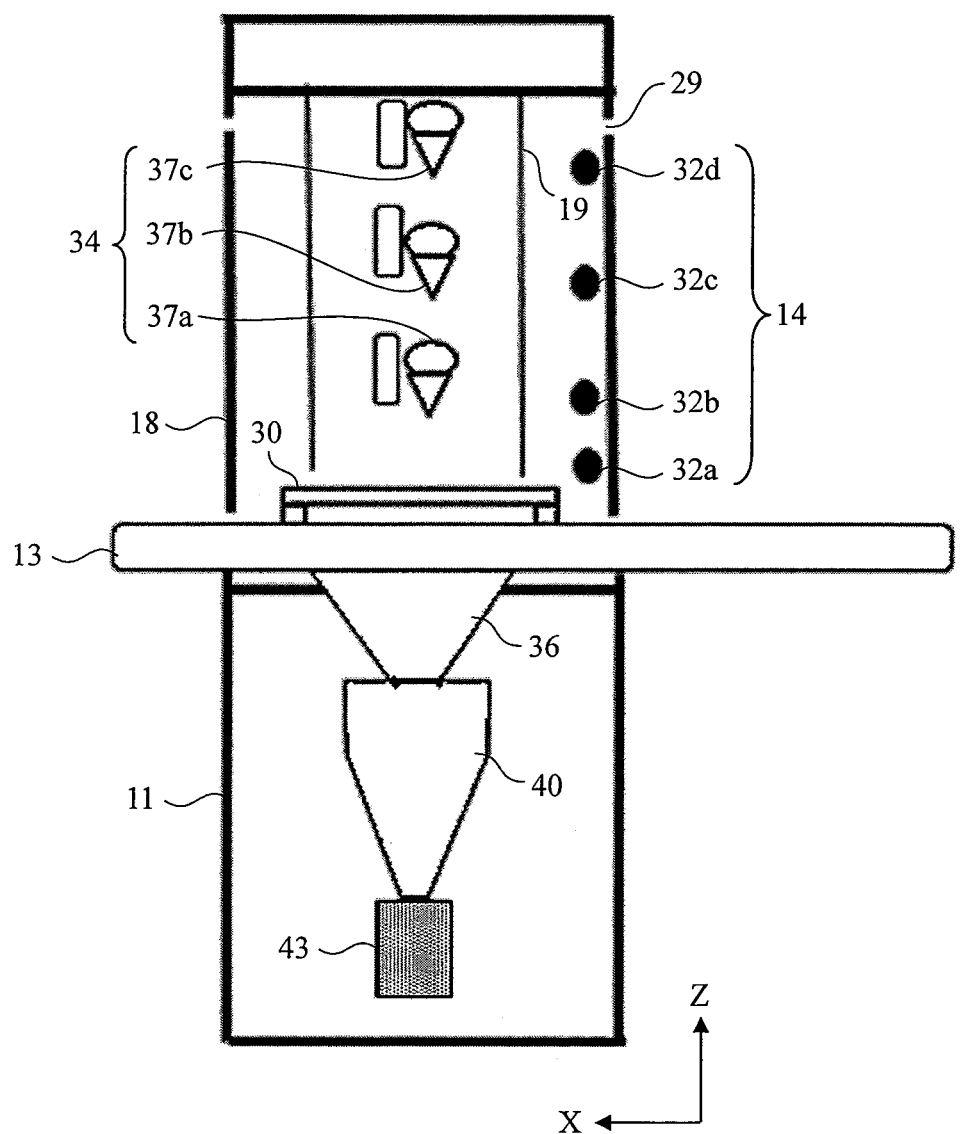
FIG. 4 is another schematic cross sectional view of the example of the peeling/collection unit.

The configuration of the peeling/collection unit 5 of the attached matter inspection device 1 according to the present embodiment will be described with reference to FIG. 3 and FIG. 4. FIG. 3 is a schematic cross sectional view taken along A-A' direction in FIG. 2. In FIG. 3, illustration of various units of the attached matter inspection device 1 other than the heating unit 22, the operation panel 7, the power supply unit 6, and the compressed air generation unit 16 is omitted. FIG. 4 is a schematic lateral cross section of the sampling chamber 18. In FIG. 4, illustration of units of the attached matter inspection device 1 other than the air nozzle unit 34, the inspection object recognition unit 14, and the delivery drive unit 13 is omitted.

The inspection object is placed on a meshed transport tray 30 and transported into the sampling chamber 18 by the delivery drive unit 13. According to the present embodiment, the size of a sampling chamber entrance 29 of the sampling chamber 18 for passing the inspection object is 60 cm in width and 64 cm in height. The sampling chamber entrance 29 is provided with the inspection object recognition unit 14. The inspection object recognition unit 14, as illustrated in FIG. 3, includes a plurality of light projectors 31a to 31d and a plurality of light receivers 32a to 32d for receiving light from the light projectors 31a to 31d, the projectors and receivers being disposed in opposite wall portions of the sampling chamber 18. The light receivers 32a to 32d of the inspection object recognition unit 14 are set to output a signal under the condition that the light from the light projectors was blocked by the inspection object and was not received by the light receivers. The signal from the light receivers 32a to 32d is transmitted via the peeling/collection unit controller 10 to the air nozzle controller 15.

In the present embodiment, the inspection object recognition unit 14 includes four pairs of the light projectors 31a to 31d and the light receivers 32a to 32d, which are disposed at intervals along the Z-direction. Specifically, in the inspection object recognition unit 14, the pairs of the light projectors and light receivers are disposed at the positions of 2 cm, 10 cm, 26 cm, and 43 cm above the delivery surface of the delivery drive unit 13.

In the sampling chamber 18, air nozzles 37a to 37c for spraying an air jet toward the surface of the inspection object are disposed on the left-side side surface of the sampling chamber inspection object with respect to the delivery direction, at the positions of 12 cm, 28 cm, and 45 cm above the delivery surface, respectively. In FIG. 4, the distance between the inspection object recognition unit 14 and the center of air jet ejection holes of the air nozzles 37a to 37c of the air nozzle unit 34 is 5 cm.

The inner surface of the sampling chamber 18 is covered with the cover 19 made from tetrafluoroethylene resin for easy cleaning. The air jet ejection holes of the air nozzle unit 34, and the light projectors 31a to 31d and the light receivers 32a to 32d of the inspection object recognition unit 14 are disposed at positions recessed from the surface of the cover 19. The wall surface of the cover 19 on the collector 36 side has a recessed shape, as illustrated in FIG. 2, where the wall surface is partly recessed in the Y-axis direction so as to ensure a space of the same area as the opening portion 35 of the collector 36. The recessed shape enables efficient introduction of the sample fine particles, peeled from the inspection object, into the opening portion 35 of the collector 36 while decreasing their dispersion into the sampling chamber 18. The opening portion 35 is fitted with a meshed filter 33 with an opening width of 3 mm for preventing the inspection object from getting caught during delivery, or the fall of small items into the collector.

The collector 36 will be described. The collector 36 is disposed at the lower end of the recess portion of the right-side wall surface of the sampling chamber 18 of the chamber as viewed in the X-axis direction in FIG. 2, below the delivery surface of the delivery drive unit 13.

The inventors have previously learned about the need for a function for suctioning the inside of the collector 36 if the sample fine particles peeled from the inspection object are to be collected. Based on this knowledge, to the bottom portion of the collector 36, an L-shaped aspiration pipe 38 is connected to aspirate the inside of the collector 36. The L-shaped aspiration pipe 38 converts the direction of the suctioned air flow from the vertical direction to the horizontal direction. At the portion where the aspiration pipe 38 and the collector 36 are connected, an easily insertable and drawable coarse filter 39 is connected so as to prevent small items, such as coins or precious metals, and fibrous dust and the like from being transported to the separation unit 12. As the coarse filter 39, a filter having an opening width of 0.2 mm is used, which is smaller than the opening width of the meshed filter 33 installed at the opening portion 35 of the collector 36. The flow-out end of the aspiration pipe 38 is connected to an outer cylinder 40 of the separation unit 12.

First, the inventors verified whether the location of the collector 36 and the air nozzle unit 34 shown in FIG. 3 was functionally effective in peeling and collecting the sample fine particles from the inspection object. The distance between the air nozzle unit 34 and the collector 36 parallel to the Y-axis in FIG. 3 was 60 cm. The size of the opening portion 35 of the collector 36 was such that the width in the X-axis direction was 30 cm each to the left and right from the nozzles at the center, for a total of 60 cm, and the width in the Y-axis direction was 15 cm. The height of the collector 36 was 41.5 cm. In an experiment, the pressure of the air jet ejected from the air nozzle unit 34 was 0.25 MPa, and the amount of aspiration by the aspiration unit 21 was 1400 liter/min.

Figures 5, 6:
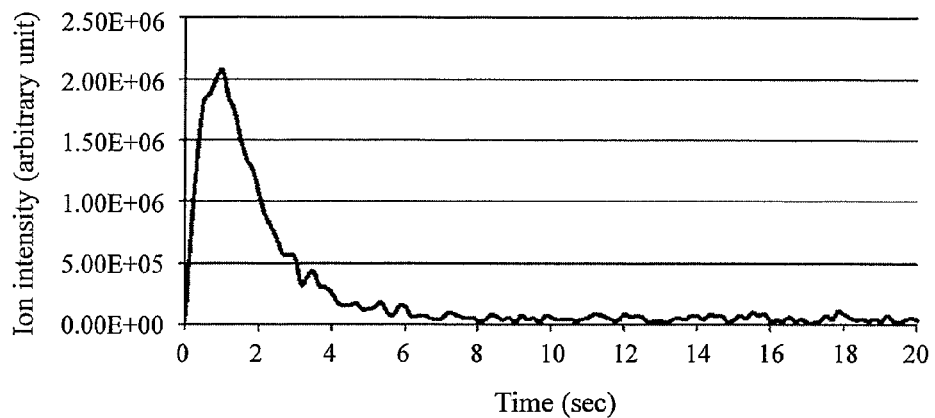
FIG. 5 is a chart illustrating a chronological change in signal intensity of a mass-to-charge ratio of a trinitrotoluene explosive component detected from an inspection object to which trinitrotoluene explosive particles are attached.
FIG. 6 is a chart illustrating the relationship between signals from an inspection object recognition unit and air nozzles used in first and third peeling steps.

FIG. 5 shows the result of an experiment of detecting explosive fine particles of trinitrotoluene from an inspection object, using the configuration of the attached matter inspection device 1 illustrated in FIG. 1. In FIG. 5, the horizontal axis shows time in seconds, and the vertical axis shows ion intensity in an arbitrary unit.

From the result of FIG. 5, it has been verified that, in the attached matter inspection device 1 in which the air nozzle unit 34 and the collector 36 are disposed as described above, a signal indicating the trinitrotoluene explosive fine particles can be detected from the inspection object with sufficient signal intensity. Specifically, it has been proved that the attached matter inspection device 1 according to the present embodiment is an effective means of peeling, collecting, and inspecting sample fine particles attached to an inspection object.

With reference to FIG. 3, the separation unit 12 of the present embodiment will be described. The separation unit 12 utilizes a cyclone phenomenon. The separation unit 12 includes an aspiration fan 41 of the aspiration unit 21, an inner cylinder 42 connected to the aspiration fan 41, and the outer cylinder 40, which has a conical shape. To the outer cylinder 40, there is connected the L-shaped aspiration pipe 38 in such a manner as to internally contact the inner periphery of the outer cylinder 40.

The aspiration fan 41 suctions, via the inner cylinder 42 and the outer cylinder 40, the air inside the collector 36 through the L-shaped aspiration pipe 38. To the smaller-diameter side of the outer cylinder 40, the heating unit 22 is connected. In the heating unit 22, there are disposed a heat block 43 for the insertion of a collection filter unit 17; a heat source 44 for heating the heat block 43 to a certain temperature and maintaining the temperature; and a thermometer 45 for measuring the temperature. The thermometer 45 for the heat block 43 and the heat source 44 are connected to the inspection unit controller 8. The heat block 43 may be heated to an arbitrary temperature between room temperature and 300° C. and maintained at the temperature.

A step of peeling fine particles from the inspection object will be described. The step of peeling the sample fine particles from the inspection object may be divided into the following three steps. The first step is a step in which the inspection object is delivered into the sampling chamber 18 and a location corresponding to a front end surface of the inspection object is bombarded with an air jet. The second step is a step of bombarding a location corresponding to an upper surface of the inspection object with an air jet. The third step is a step of bombarding a location corresponding to a rear end surface of the inspection object with an air jet.

The inventors have experimentally learned that in order to effectively peel explosive fine particles attached to an inspection object, it is effective to bombard the inspection object surface with an air jet intermittently. Based on this knowledge, bombardment or ejecting is defined according to the present embodiment as an operation in which a cycle of ejecting the air jet for 0.1 second and then stopping the ejecting for 0.1 second is repeated, rather than a continuous ejecting of air jet.

In the following, an operating condition of the air nozzle unit 34 for performing the above-described peeling step after the inspection object is transported into the sampling chamber 18 will be described with reference to FIG. 6 and FIG. 7.

In the present embodiment, when the size of the inspection object is determined by the inspection object recognition unit 14, only the air nozzles allocated in accordance with that size are operated. FIG. 6 shows the air nozzles operated in the first step and the third step in the peeling step. FIG. 7 shows the air nozzles operated in the second step.

Figures 7, 8:
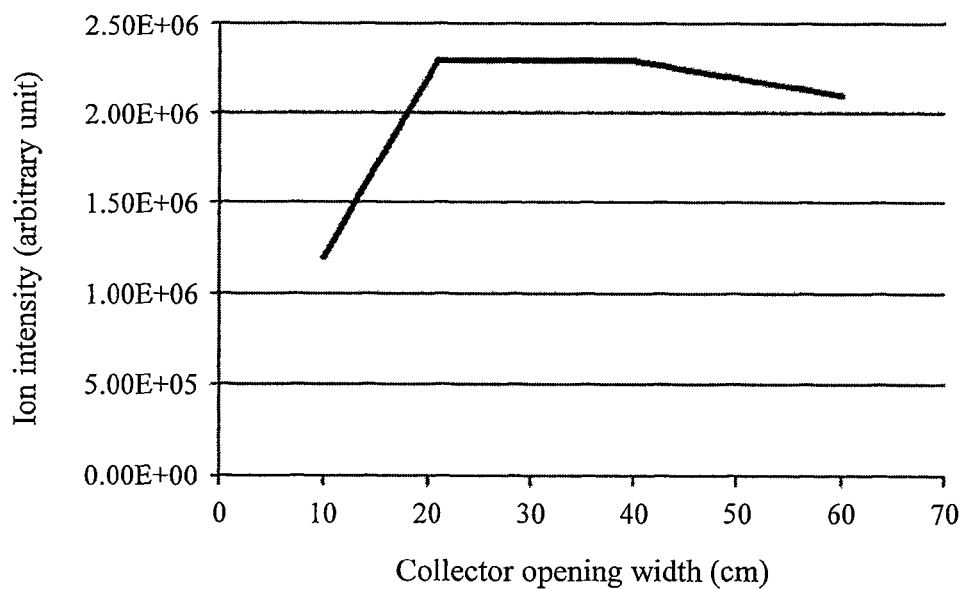
FIG. 7 is a chart illustrating the relationship between the signals from the inspection object recognition unit and air nozzles used in a second peeling step.
FIG. 8 is a chart illustrating the relationship between the signal intensity of the mass-to-charge ratio of the trinitrotoluene explosive component and the opening width of a collector.

Referring to FIG. 7, when a signal is output from the light receiver 32c, for example, the air nozzles 37b and 37c in the columns noted with "eject" in the row of 32c are operated. Namely, the air nozzles 37b and 37c at positions enabling the bombardment of the upper surface of the inspection object with an air jet are operated, while the air nozzle 37a that is not at a position enabling the bombardment of the upper surface of the inspection object with an air jet is not operated.

The following description of the peeling step is based on the condition that the light receiver 32c has output the signal.

In the first step, based on the operation chart for the inspection object recognition unit 14 and the air nozzle unit 34 shown in FIG. 6, because the light receiver 32c has output the signal, the air nozzles 37a to 37c are prepared for operation as described above.

In FIG. 4, the distance between the position of the inspection object recognition unit 14 and the center of the ejection holes of the air nozzle unit 34 is 5 cm. The delivery speed of the delivery drive unit 13 is 12 m/min. Thus, the time it takes for the inspection object to reach the center of the ejection holes of the air nozzle unit 34 after passing the inspection object recognition unit 14 is 2.5 seconds.

In the first step, two seconds after the inspection object is sensed by the inspection object recognition unit 14, the inspection object is bombarded with an air jet via the air nozzles 37a to 37c for one second. The timing is such that the air jet is ejected starting from a position one centimeter before the front end surface of the sensed inspection object. Thus, a location corresponding to the front end surface of the inspection object can be reliably bombarded with the air jet.

In the second step, based on the operation chart for the inspection object recognition unit 14 and the air nozzle shown in FIG. 7, the air nozzles 37b and 37c are prepared for operation. Following the first step, the air nozzles 37b and 37c repeat the ejecting until the inspection object passes the inspection object recognition unit 14.

In the third step, the same air nozzles as those of the first step, i.e., the air nozzles 37a to 37c, are used. Following the second step, after the inspection object has passed the inspection object recognition unit 14, the air nozzles 37b and 37c continuously perform the air jet bombardment. Two seconds after the inspection object has passed the inspection object recognition unit 14, air jet bombardment from the air nozzles 37a to 37c is started. In the third step, the air jet bombardment from the air nozzles 37a to 37c is continued for three seconds after the inspection object has passed the inspection object recognition unit 14, and then stopped.

In the peeling step according to the present embodiment, the air jet is intermittently ejected, whereby sample fine particles can be peeled from the inspection object efficiently with a low consumption of compressed gas.

The inventors have also learned from past experiments that, in order to peel and collect sample fine particles from the inspection object, it is effective to use a means of suctioning an amount of air not less than the air amount of the air jet ejected onto the inspection object and the volume of the collector 36.

As described above, in the attached matter inspection device 1 illustrated in FIG. 2, it is desirable to minimize the size of the aspiration fan 41 used in the aspiration unit 21 for the sake of compatibility with the existing X-ray transmission inspection device in terms of device size (width, height dimension, and the height dimension of the delivery drive surface). In order to reduce the amount of the peeled sample fine particles that become attached to or deposited on the inner wall of the collector 36, it is also desirable to minimize the surface area of the inner wall of the collector 36, and to minimize the inclination angle of the inner wall relative to the direction of gravity. Based on this understanding, the inventors first experimentally determined the size of the opening portion 35 of the collector 36 that enables efficient collection of the sample fine particles peeled from the inspection object.

FIG. 8 shows the result of an experiment of peeling and collecting trinitrotoluene explosive fine particles from an inspection object using the configuration of the attached matter inspection device 1 shown in FIG. 1, while the width of the collector opening portion 35 in the X-axis direction was varied symmetrically to the left and right from the center of the air nozzle unit 34. The depth length of the collector opening portion 35 in the Y-axis direction was determined on the assumption that the width of the attached matter inspection device 1 was equivalent to the width of existing, conventional X-ray transmission inspection devices, or 100 cm, and by inversely calculating a depth length permissible for the collector 36 based on the width value. In the present embodiment, the depth length of the collector opening portion 35 in the Y-axis direction is 15 cm. For similar reasons, the distance between the installed position of the air nozzle unit 34 and the collector opening portion 35 is 60 cm.

In FIG. 8, the horizontal axis shows the width of the collector opening portion 35 in the X-axis direction in centimeters, and the vertical axis shows ion intensity in an arbitrary unit. From the result of FIG. 8, it has been learned that when the air nozzle unit 34 and the collector 36 are disposed as according to the present embodiment, not much difference is observed in the trinitrotoluene explosive detection intensity when the width of the collector opening portion 35 in the X-axis direction is approximately 20 cm or greater.

In view of the above result, the inventors, using the configuration of the attached matter inspection device 1 shown in FIG. 1, determined the width of the collector opening portion 35 in the X-axis direction to be 20 cm, and the depth length in the Y-axis direction to be 15 cm. Then, the inventors, in order to experimentally determine the height of the collector 36 such that the sample fine particles peeled from the inspection object can be efficiently collected, conducted an experiment of peeling and collecting trinitrotoluene explosive from the inspection object while varying the volume of the collector 36.

Figure 9:
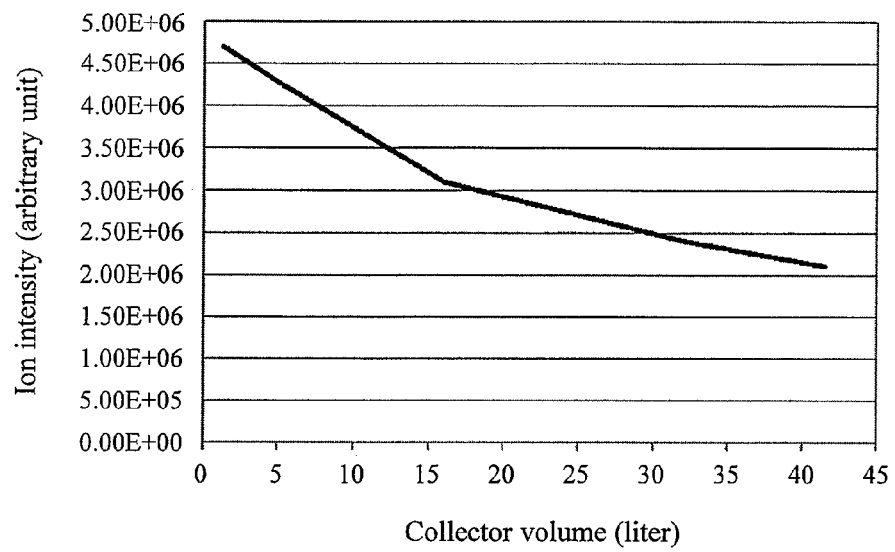
FIG. 9 is a chart illustrating the relationship between the signal intensity of the mass-to-charge ratio of the trinitrotoluene explosive component and the collector volume.

FIG. 9 shows the result of the experiment. In FIG. 9, the horizontal axis shows the volume of the collector 36 in liters, and the vertical axis shows ion intensity in an arbitrary unit. From the result of FIG. 9, it has been learned that the smaller the volume of the collector 36, the higher the detection intensity of the trinitrotoluene explosive obtained tends to become.

From the experiment result, the collector 36 of the attached matter inspection device 1 according to the present embodiment was provided with a tapered shape with a width of the collector opening portion 35 in the X-axis direction of 20 cm, a depth length in the Y-axis direction of 15 cm, a height in the Z-axis direction of 13.5 cm, and a diameter of the L-shaped aspiration pipe 38 connected to the bottom portion of the collector 36 of 3 cm. The inner wall of the collector 36 is smoothly covered with a tetrafluoroethylene cover. The collector 36 had a volume of approximately 1.3 liters, and a surface area of the inner wall of approximately 467 cm$^2$, which are respectively approximately 1/30 and 1/8 of the collectors according to Patent Literatures 1 to 3.

By using the collector 36 of the small size according to the present invention, the surface area of the walls of the collector 36 can be decreased. Thus, the probability of the sample fine particles becoming attached to or deposited on the wall surface of the collector 36 while being transported in the collector 36 can be decreased. Further, the area of the surface parallel with the collector opening portion 35 can also be decreased, increasing the flow velocity of the air flow in the collector 36 caused by aspiration by the aspiration fan 41. As a result, the transport speed of the sample fine particles transported by the air flow in the collector 36 is also increased, further decreasing the probability of the sample fine particles becoming attached to or deposited on the wall surfaces forming the collector 36. Thus, the sample fine particles that flew to the collector opening portion 35 can be efficiently and quickly suctioned into the L-shaped aspiration pipe 38.

The sample fine particles drawn into the aspiration pipe 38 are transported into the outer cylinder 40 of the separation unit 12 together with air. Together with the air aspirated at this time, the attached substance peeled from the inspection object and dust and the like are also suctioned. Dust, which has a large shape compared with explosive substance, is collected by the coarse filter 39, and only smaller substance such as the attached substance is transported into the separation unit 12 together with the air.

According to the present embodiment, the amount of aspiration of the outer cylinder 40 by the aspiration fan 41 is controlled by the peeling/collection unit controller 10 so that the flow velocity at the connection opening between the outer cylinder 40 of the separation unit 12 and the aspiration pipe 38 becomes approximately 12 m/s at which a cyclone phenomenon can be caused in the outer cylinder 40. The air including the attached substance aspirated by the aspiration fan 41 forms a swirling current that descends along the outer periphery of the inner surface of the conical outer cylinder 40. The flow of the swirl reaches vicinity of the lower portion of the outer cylinder 40, suctioned by the inner cylinder 42, and then discharged out of the aspiration fan 41 via a dust scattering prevention filter. At this time, the sample fine particles settle into the lower portion of the outer cylinder 40 along the inner surface of the outer cylinder 40, and collected on the surface of the collection filter unit 17 in the heating unit 22 connected to the lower portion of the outer cylinder 40.

The inventors observed the particle size of actual explosives, and have learned that their minimum size is 10 to 20 micrometers. From this knowledge, according to the present embodiment, the collection filter unit 17 uses an impermeable stainless steel filter with excellent heat resistance and durability and of a roughness with an opening of 12.7 micrometers. Because the filter is impermeable, particles of 10 to 20 micrometers can be caught.

The collection filter unit 17 is inserted into the heat block 43 that is being heated. Thus, the collection filter unit 17 is also heated to a temperature equivalent to the heat block 43. Accordingly, the sample fine particles attached to the collection filter unit 17 are also rapidly heated, whereby quick vaporization of the sample fine particles is promoted and sample gas is generated.

Figure 10:
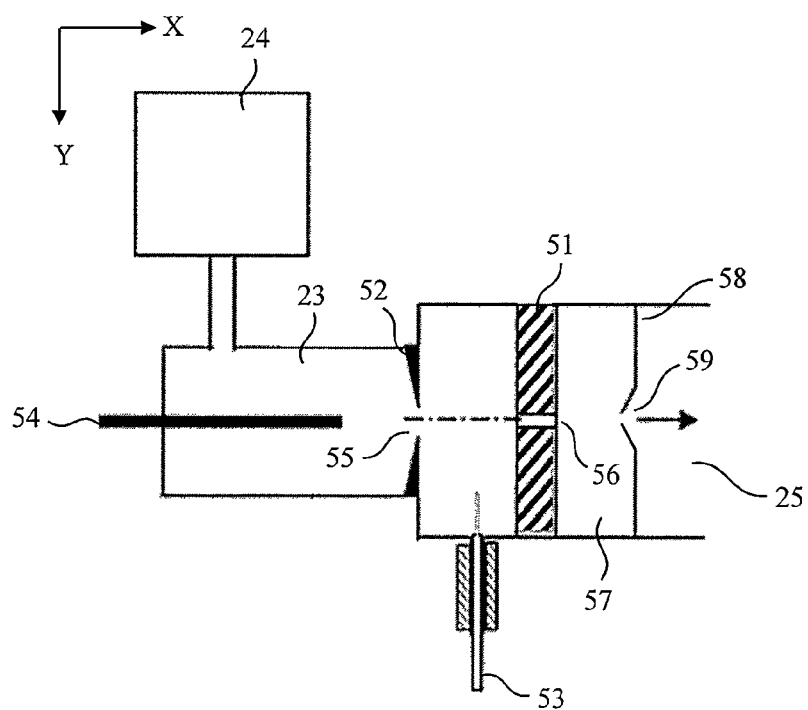
FIG. 10 is a diagram of the configuration of an ion source unit.

FIG. 10 is a top view illustrating the configuration of the ion source unit 23 of the attached matter inspection unit 2. In FIG. 10, illustration of the units of the attached matter inspection device 1 other than the ion source unit 23 is omitted.

The sample gas generated in the heat block 43 is caused to pass through an introduction piping 53 by the suction pump 24 and carried to a space between a first electrode 51 having a thin opening and an opposite electrode 52 of the ion source unit 23. The ion source unit 23 and the introduction piping 53 are provided with a heat source and a thermometer. Electric power supply to the heat source is controlled by the inspection unit controller 8 on the basis of an output signal from the thermometer. The ion source unit 23 and the introduction piping 53 are heated to and maintained at a desired temperature at all times so that the vaporized sample would not become adsorbed on the inside of the ion source unit 23.

In the ion source unit 23, a needle electrode 54 is disposed. Between the needle electrode 54 and the opposite electrode 52, a high voltage is applied to generate corona discharge around the tip of the needle electrode 54, whereby nitrogen, oxygen, water vapor and the like are initially ionized. These ions are referred to as primary ions. The primary ions are moved by an electric field toward the opposite electrode 52. The vaporized sample carried to the space between the first electrode 51 having a thin opening and the opposite electrode 52 flows via an opening portion 55 provided in the opposite electrode 52 into the space in which the needle electrode 54 is disposed. In this space, the vaporized sample reacts with the primary ions and thereby ionized. The method of generating the primary ions using corona discharge in atmosphere and ionizing a chemical substance in a gas using chemical reaction of the primary ions and the gas is referred to as an atmospheric pressure chemical ionization method.

Between the opposite electrode 52 and the first electrode 51 having a thin opening, there is a potential difference on the order of 1 kV. Thus, the ions are moved toward the first electrode 51 having a thin opening, and then taken into a differential evacuation portion 57 via a first ion introducing thin opening 56. In the differential evacuation portion 57, adiabatic expansion occurs, causing so-called clustering in which solvent molecules and the like are attached to the ions. In order to reduce the clustering, it is desirable to heat the first electrode 51 having a thin opening and a second electrode 58 having a thin opening using a heater and the like.

The sample ions generated by the atmospheric pressure chemical ionization method are introduced into the mass analysis unit 25 via the first ion introducing thin opening 56 of the first electrode 51 having a thin opening, the differential evacuation portion 57 evacuated by an evacuation system which is not shown, and a second ion introducing thin opening 59 of the second electrode 58 having a thin opening. The mass analysis unit 25 is evacuated by the evacuation unit 26. The ion source unit 23 and the mass analysis unit 25 constitute a single container.

The sample ions introduced into the mass analysis unit 25 are subjected to mass analysis using an ion trap mass spectrometer. In the data processing unit 27, values of mass-to-charge ratios necessary for identifying one or a plurality of attached substances to be detected are set in advance. An output signal from a detector of the mass spectrometer with regard to a mass-to-charge ratio necessary for identifying the attached substance to be detected is sent to the data processing unit 27 consecutively at predetermined time intervals as a sample ion mass analysis result, and subjected to data processing. In a storage means of the data processing unit 27, there is stored a database of mass analysis data (mass-to-charge ratio values and relative intensities) required for identifying a plurality of attached substances, such as explosives and chemical drugs, and signal intensity determination threshold values as a reference for determining the identity of the attached substance. The mass-to-charge ratio of the signal sent to the data processing unit 27 is compared with the database read from the storage means and identified as the stored mass-to-charge ratio of a certain attached substance. If the intensity of the received signal is greater than the determination threshold value, the probability of presence of the attached substance is displayed on the operation panel 7 to notify the operator.

Figure 11:
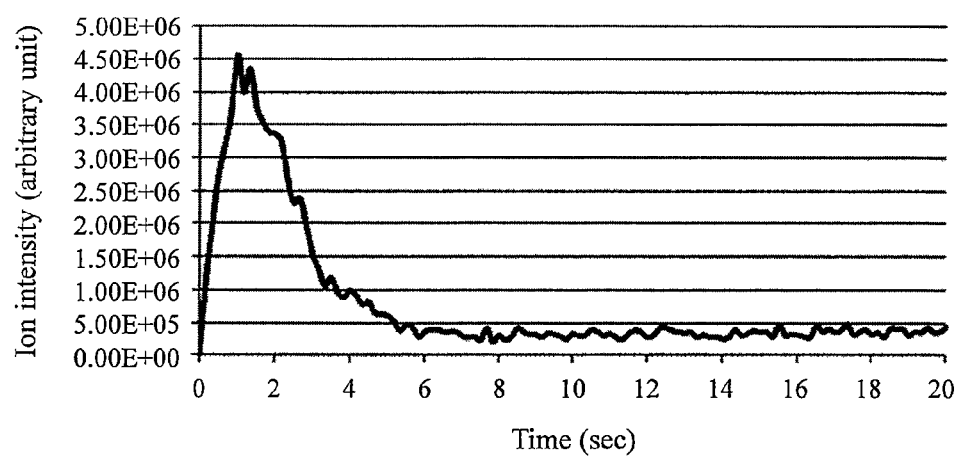
FIG. 11 is a chart illustrating a chronological change in the signal intensity of the mass-to-charge ratio of the trinitrotoluene explosive component detected from an inspection object to which trinitrotoluene explosive particles are attached.

FIG. 11 shows the result of inspection of an inspection object to which trinitrotoluene explosive particles were attached, using the configuration of the attached matter inspection device illustrated in FIG. 2. In FIG. 11, the vertical axis shows the signal intensity in an arbitrary unit, and the horizontal axis shows time in seconds.

As shown in FIG. 11, a clear signal is obtained indicating the detection of a trinitrotoluene explosive component. Based on the result, it has been proved that by using the attached matter inspection device 1 equipped with the small-sized collector, trinitrotoluene explosive particles can be peeled, using an air jet, from an actual inspection object to which the trinitrotoluene explosive particles are attached, collected by the collection filter unit 17, and vaporized by the heat block 43, followed by sensing the trinitrotoluene explosive component using the mass analysis unit 25.

In the attached matter inspection device 1 according to the present embodiment described above, it can be inspected under a certain condition whether an attached substance such as an explosive is included in the sample fine particles attached to the inspection object without contact with the inspection object and automatically. Thus, a quick inspection can be performed without causing damage or contamination and the like in the inspection object, and without requiring a trained attendant.

Further, in the attached matter inspection device 1 with the air nozzle unit 34 and the collector 36 located according to the present embodiment, the opening portion 35 of the collector 36 may be small, and the collector 36 may be of a small size with a small volume. Thus, for the above-described reasons, the probability of the sample fine particles peeled from the inspection object becoming attached to or deposited on the inner wall of the collector 36 can be decreased. Further, as a suction means inside the collector 36 that is required for collecting the sample fine particles, the aspiration fan 41 with small aspiration capability can be used, which is effective in decreasing the size of the attached matter inspection device, electric power consumption, and noise. In addition, because a belt-type delivery means used in conventional X-ray transmission inspection devices may be used, the risk of the inspection object being caught or small items accidentally dropping into the collector 36 can be made extremely low. As a result, an attached matter inspection device with high operation rate and reliability can be realized.

The inventors have also experimentally discovered that the sample fine particles that have once been peeled from the inspection object can be easily peeled again by spraying an air jet with low wind speed on the order of several m/s. It has also been discovered that explosive fine particles remain on the inner wall of the collector 36 after the explosive fine particles are detected.

If the next inspection object is inspected with the attached matter fine particles, such as explosive fine particles, remaining on the inner wall of the collector 36, the attached matter fine particles remaining on the inner wall of the collector 36 may be peeled again and become collected in the collection filter unit 17. In this case, the attached matter may be sensed even though there is actually no attached matter fine particles attached to the inspection object, causing an erroneous detection. Thus, it has been learned that a self-cleaning function for the collector 36 is indispensable in the attached matter inspection device 1.

As a cleaning means for the inner wall of the collector 36, the trained attendant may carefully wipe the inner wall of the collector 36 using a clean wiping material. However, this method is not realistic in view of the attendant's safety, the time required for the cleaning or replacement, and the possible human contamination of the inner wall of the collector 36. Thus, it is necessary to provide the attached matter inspection device 1 with a function for automatically cleaning the inner wall of the collector 36.

The self-cleaning function have the issues of 1) how to minimize the time for self-cleaning so that inspection can be resumed swiftly, and 2) how to quantitatively confirm the cleaning effect so as to prevent erroneous detection.

The attached matter inspection device 1 illustrated in FIG. 3 is provided with a line air blower 46 for self-cleaning purpose. The line air blower 46 blows a linear air jet to the recessed portion of the cover 19 installed on the inner wall of the sampling chamber 18 on the collector 36 side, and to the opening portion 35 of the collector 36.

The self-cleaning of the attached matter inspection device 1 according to the first embodiment is performed in accordance with the following procedure.

When it is determined in the data processing unit 27 that an explosive component has been detected from the inspection result, the attendant is notified via a display on the operation panel 7. The attached matter inspection device 1 then enters a stand-by state for an instruction for starting the self-cleaning. When a self-cleaning execution instruction is selected by the attendant via the operation panel 7, the central control unit 3 issues a self-cleaning step instruction to the peeling/collection unit controller 10 and the inspection unit controller 8.

In the peeling/collection unit controller 10, the normal inspection step is stopped and a predetermined self-cleaning step is started. The self-cleaning step is executed as follows. The aspiration fan 41 is driven to aspirate the inside of the collector 36, and linear air jets are emitted from the air nozzle unit 34 and the line air blower 46 toward the recessed portion of the cover 19 and the collector opening portion 35, respectively. The explosive fine particles remaining in the recessed portion of the cover 19 and the collector 36 are peeled again by the linear air jet bombardment, transported to the separation unit 12 by the suctioning by the aspiration fan 41, and then collected in the collection filter unit 17. This cycle constitutes a single self-cleaning step.

Next, a self-inspection step is performed to determine whether the same level of cleanliness as before the detection of the explosive fine particles by the attached matter inspection device 1 has been recovered.

After the single self-cleaning step is completed, the component detected from the collection filter unit 17 is compared with an explosive fine particles component stored in advance. If it is determined as a result of the comparison that the same level as before the detection of the signal of the explosive by the attached matter inspection unit 2 is achieved, the normal inspection step is resumed. If it is determined that the level is that of detection of the explosive signal, the self-cleaning step is started again.

By the self-cleaning means according to the present embodiment described above, the attached matter inspection device 1 can be cleaned automatically and in a short time even after the attached substance such as an explosive has been sensed from the inspection object. By inspecting the cleanliness of the cleaned collector 36 by the attached matter inspection unit 2, the cleaning effect can be quantitatively confirmed. Thus, erroneous detection by an inspection even after the attached matter has been sensed can be eliminated. The measurement of the self-cleaning effect may not be implemented for each self-cleaning step. By performing the self-cleaning effect measurement at the end of a predetermined number of times of self-cleaning, the required time for self-cleaning can be decreased.

In the attached matter inspection device 1 according to the present embodiment described above, the air jet bombardment by the air nozzle unit 34 is performed at a surface of the inspection object above the delivery drive surface. However, by providing an air nozzle that bombards a lower surface of the inspection object with an air jet, attached matter inspection can be performed with respect to a wider surface of the inspection object.

Figure 12:
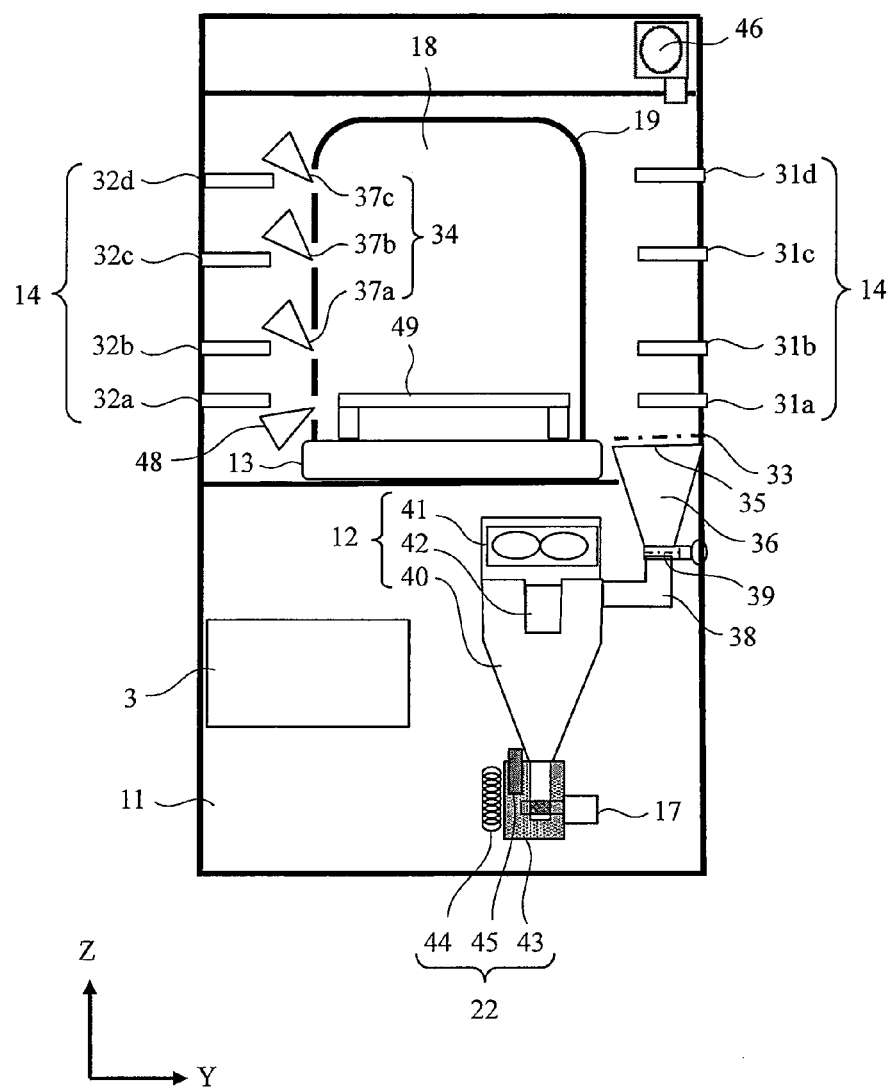
FIG. 12 is a schematic cross sectional view of another example of the peeling/collection unit.

FIG. 12 is a schematic view of an embodiment of the attached matter inspection device 1 newly provided with a lower nozzle 48 for bombarding a surface of the inspection object lower than the delivery drive surface with an air jet.

In the attached matter inspection device 1 according to the present embodiment, the inspection object is mounted on a legged tray 49 so that a space can be formed between the inspection object and the delivery drive surface for the passage of air jet. In the following, a step for peeling the sample fine particles from the inspection object in the attached matter inspection device 1 provided with the lower nozzle 48 will be described. In the following, the peeling step will be described under the condition that the light receiver 32c has output a signal.

In a first step, in view of the operation chart for the inspection object recognition unit 14 and the air nozzle unit 34 shown in FIG. 6, because the light receiver 32c has output the signal, the nozzles 37a, 37b, and 37c are prepared for operation as described above. In the first step, the air nozzles emit an air jet for one second starting from two seconds after the inspection object is sensed by the inspection object recognition unit 14.

In a second step, in view of the operation chart for the inspection object recognition unit 14 and the nozzles as shown in FIG. 7, because the light receiver 32c has output the signal, the nozzles 37b and 37c and newly the lower nozzle 48 are prepared for operation as described above. In the second step, the lower nozzle 48 is operated at all times irrespective of the signal output condition of the light receiver 32 of the inspection object recognition unit 14.

Following the first step, the nozzles 37b and 37c and the lower nozzle 48 repeat the ejecting until the inspection object passes the inspection object recognition unit 14.

In a third step, the same air nozzles as those of the first step, namely, the nozzles 37a, 37b, and 37c, are used. Following the second step, after the inspection object has passed the inspection object recognition unit 14, the nozzles 37b and 37c continuously perform the air jet bombardment. Two seconds after the inspection object has passed the inspection object recognition unit 14, the nozzle 37a performs air jet bombardment for one second, and then the ejecting of all air jets is completed.

By performing the above peeling step, the sample fine particles can also be peeled and collected from the lower surface of the inspection object and then inspected in the attached matter inspection device 1.

In the attached matter inspection device 1 according to the present embodiment described above, the direction of the ejection holes of the air nozzle unit 34 is constant. However, one air nozzle may be provided with a plurality of ejection holes each configured to eject an air jet in a different direction, or the air nozzle may be configured to be movable.

Figure 13:
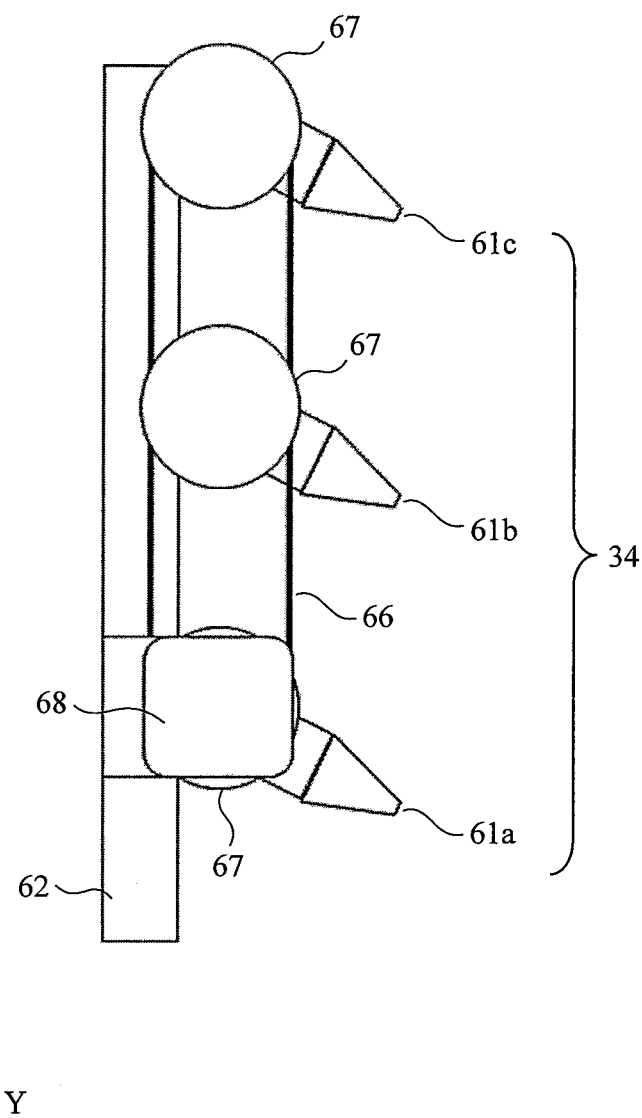
FIG. 13 is a front view illustrating the configuration of an air nozzle unit with a rotating function.
Figure 14:
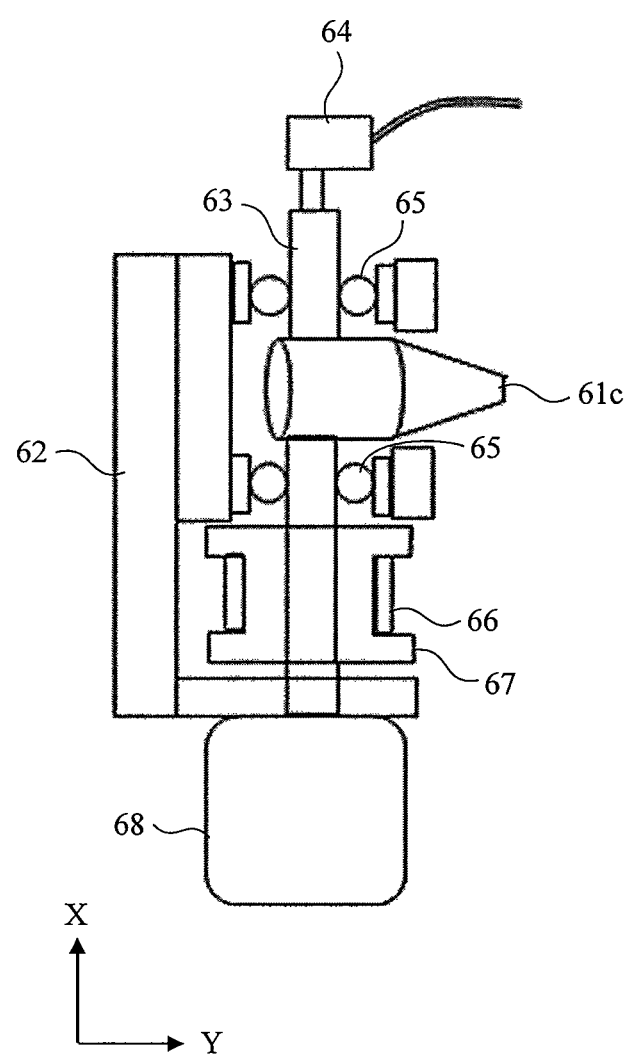
FIG. 14 is a top view illustrating the configuration of the air nozzle unit with the rotating function.

FIG. 13 and FIG. 14 are schematic diagrams of an embodiment of the air nozzle unit 34 in which the air nozzles are fitted with rotating function. Illustration of various units other than the air nozzle unit 34 is omitted. FIG. 13 is a front view as seen in the X-axis direction of FIG. 2. FIG. 14 is a top view seen from the Z-axis direction.

To one end of rotating axes 63 of the air nozzles 61a, 61b, and 61c, a rotary joint 64 capable of supplying gas to the rotating air nozzles 61a, 61b, and 61c is connected. The air nozzles 61a, 61b, and 61c are held to a holder member 62 via freely rotatable bearings 65. To the other end of the rotating axes 63 of the air nozzles 61a, 61b, and 61c, pulleys 67 are held with a belt 66 extended across the pulleys 67. Further, to the air nozzles 61a, 61b, and 61c, a rotary drive member 68 for rotating the belt 66 is coupled. The rotary drive member 68 and the bearings 65 are fixed to the holder member 62. The holder member 62 is fixed within the sampling chamber 18. In the present implement, the air nozzles 61a, 61b, and 61c are rotated in anticlockwise direction about an axis (X-axis) perpendicular to the sheet of the drawing of FIG. 13.

In the present embodiment, the time of air jet bombardment from the air nozzles 61a, 61b, and 61c is controlled to 0.1 second by the peeling/collection unit controller 10. The air nozzles are rotated by an angle of 90° in the 0.1 second period of air jet bombardment. In the remaining 270° angle rotation, no air jet bombardment is performed. Thus, the rotary drive member 68 may be rotated continuously at the rate of 150 rotations per minute constantly in one direction, eliminating the need for a special control means for rotation control. According to the present embodiment, the inspection object is ejected with an air jet while the air nozzle 61 is rotated, whereby a wider area of the inspection object can be bombarded with the air jet. Accordingly, the attached matter inspection of the inspection object can be performed in greater detail in the attached matter inspection device 1.

Second Embodiment

Figure 15:
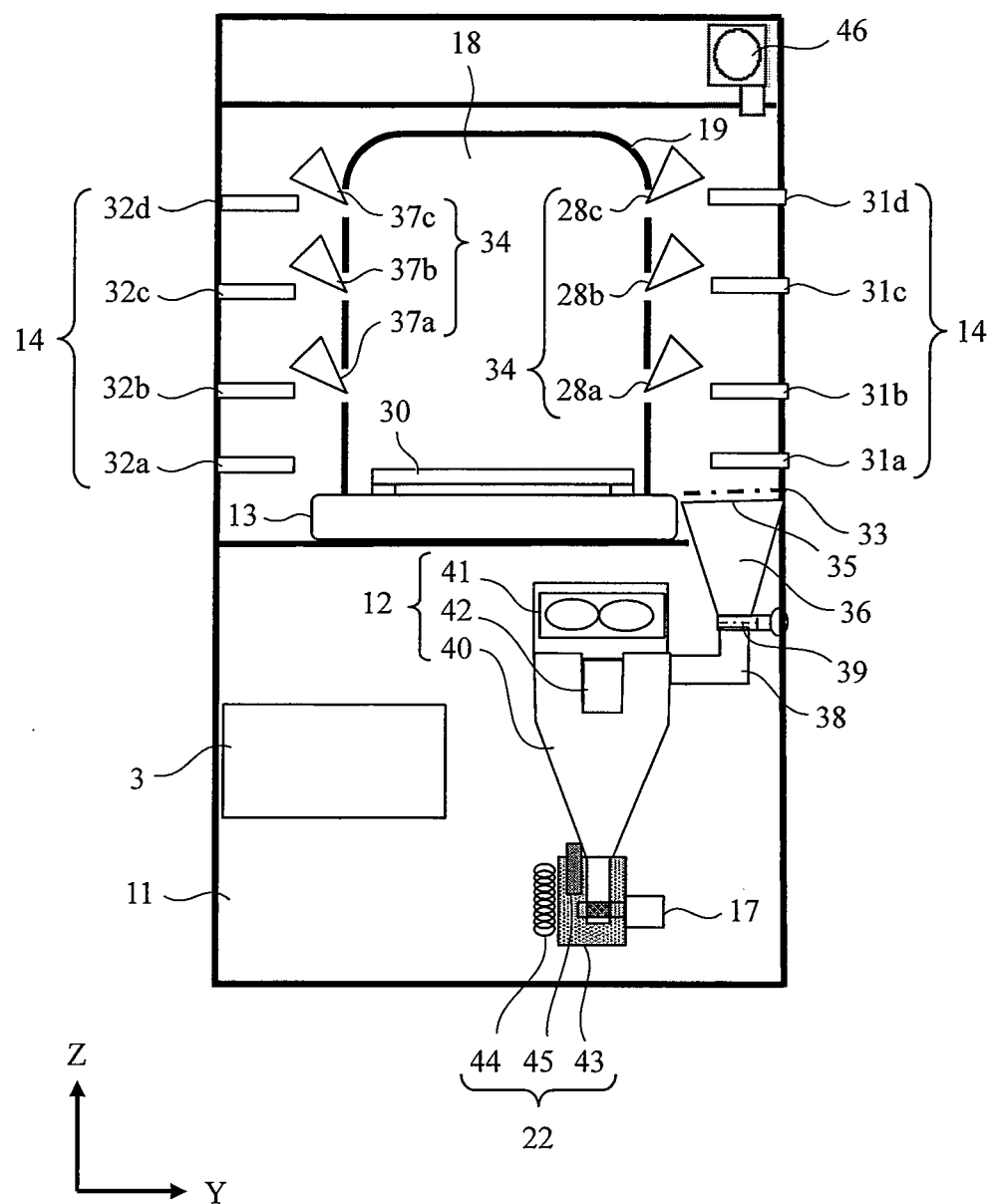
FIG. 15 is a schematic cross sectional view of another example of the attached matter inspection device according to the present invention.

FIG. 15 is a schematic diagram of the attached matter inspection device according to a second embodiment of the present invention, corresponding to a cross section taken along line A-A' of FIG. 2. In the attached matter inspection device according to the present embodiment, the air nozzle unit 34 is also provided on the wall surface of the sampling chamber 18 on the collector 36 side in addition to the location according to the first embodiment.

The step of peeling the sample fine particles from the inspection object according to the present embodiment can be divided into the following four steps.

A first step is a step of bombarding a location corresponding to the front end surface of the inspection object with an air jet. A second step is a step of bombarding a location parallel with the inspection object transport direction and corresponding to a direction perpendicular to the delivery drive surface. A third step is a step of bombarding a location corresponding to the upper surface of the inspection object with an air jet. A fourth step is a step of bombarding a location corresponding to the rear end surface of the inspection object with an air jet.

In the following, an operation for performing the peeling step after the inspection object is transported into the sampling chamber 18 will be described.

In the present embodiment, when the size of the inspection object is determined by the inspection object recognition unit 14 as described above, the air nozzles allocated in accordance with the previously determined size of the inspection object are operated. FIG. 16 to FIG. 18 show the air nozzles operated in accordance with the output from the light receiver 32 of the inspection object recognition unit 14. FIG. 16 shows the air nozzles operated in the first step and the fourth step. FIG. 17 shows the air nozzles operated in the second step. FIG. 18 shows the air nozzles operated in the third step.

In the following, the peeling step will be described under the condition that the light receiver 32c has output a signal.

In the first step, in view of the operation chart for the inspection object recognition unit 14 and the air nozzles shown in FIG. 16, because the light receiver 32c has output the signal, the air nozzles 37a, 37b, and 376c are prepared for operation. In the first step, air jet bombardment is performed for one second starting from two seconds after the inspection object is sensed by the inspection object recognition unit 14.

In the second step, air jet ejection performed from the air nozzles 37a, 37b, and 37c and the air nozzles 28a, 28b, and 28c. At this time, the air jet ejection is performed for one cycle.

In the third step, after the second step, air jet bombardment is performed from the air nozzles 37b and 37c. At this time, the air jet ejection is performed for one cycle.

The second step and the third step are performed by repeating the cycle until the inspection object passes the inspection object recognition unit 14.

In the fourth step, air jet bombardment from the air nozzles 37b and 37c is continuously performed. Two seconds after the inspection object has passed the inspection object recognition unit 14, air jet bombardment from the air nozzle 37a is performed for one second and then the ejecting of all air jets is completed.

In the second step, while some of the sample fine particles peeled by the air jet are collected in the collector 36 directly, some of the sample fine particles are deposited on the delivery drive surface. As described above, the sample fine particles that have once been peeled can be easily peeled again by air jet bombardment with small flow velocity and transported. Thus, the sample fine particles deposited on the delivery drive surface are transported to the collector opening portion 35 by the air jet ejected in the direction of the collector 36 in the third step and collected.

By performing the peeling step according to the present embodiment, attached matter inspection can be performed with respect to almost all of the surfaces of the inspection object.

Figure 19:
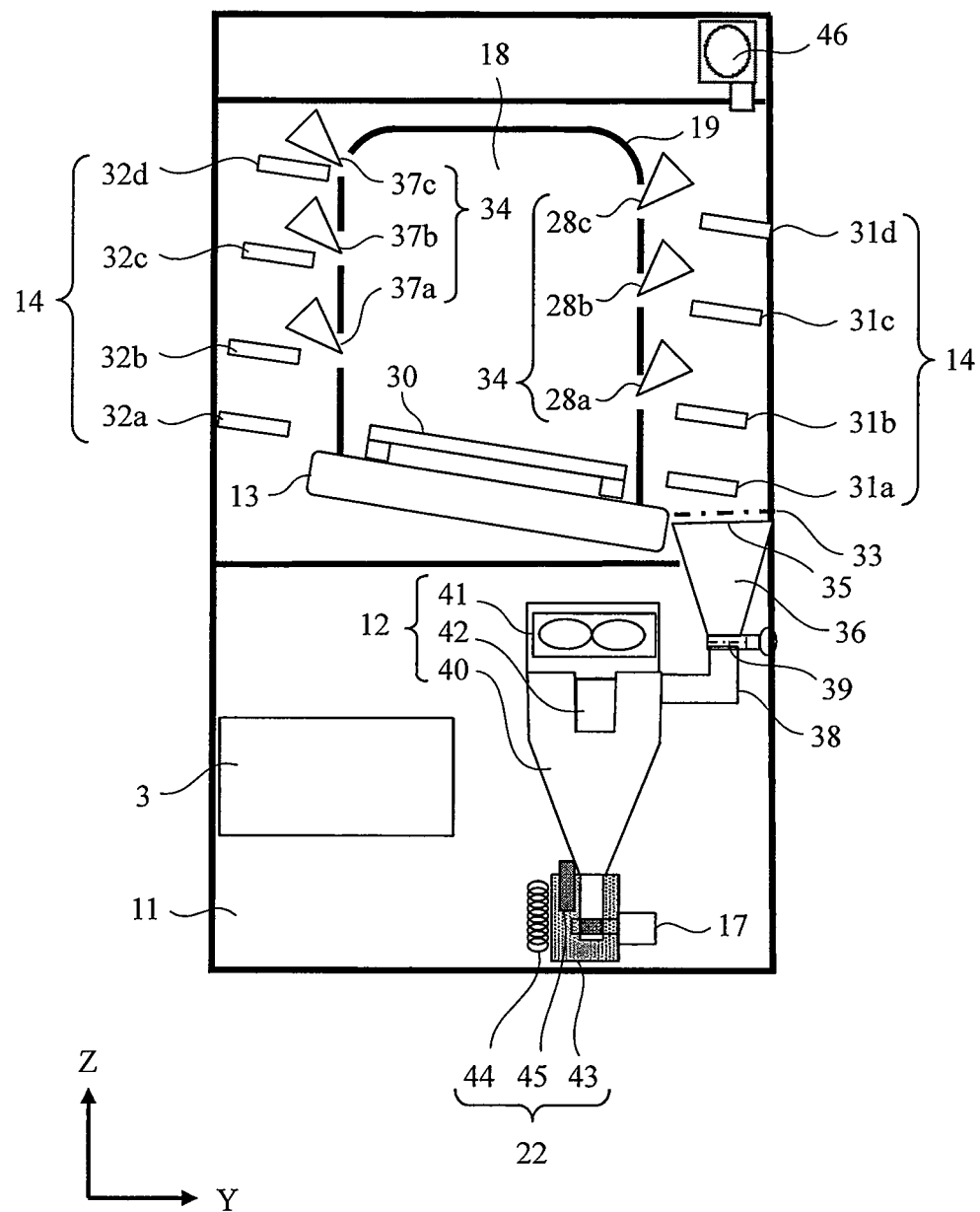
FIG. 19 is a schematic cross sectional view of an example of the attached matter inspection device with an inclined delivery drive surface.

In the present embodiment, as illustrated in FIG. 19, the delivery drive surface may be inclined toward the collector 36, whereby the sample fine particles from the inspection object may be more efficiently peeled and collected. When the delivery drive surface is inclined toward the collector 36, the inspection object is transported in the sampling chamber 18 while being pulled in the inclined direction of gravity. Thus, the positional relationship between the air nozzles 28a, 28b, and 28c and the inspection object becomes substantially constant at all times. Accordingly, the condition of the air jet with which the inspection object is bombarded also becomes substantially constant, whereby the condition for peeling of the sample fine particles from the inspection object becomes constant, enabling the sample fine particles to be peeled from the inspection object effectively. Further, the positional relationship between the inspection object and the collector opening portion 35 during air jet bombardment can be made substantially constant at all times, so that the sample fine particles peeled from the inspection object can be efficiently taken in by the collector 36.

Thus, in the attached matter inspection device 1 according to the present embodiment, the sample fine particles can be effectively peeled from the inspection object and efficiently collected, enabling more detailed attached matter inspection of the inspection object.

Third Embodiment

Figure 20:
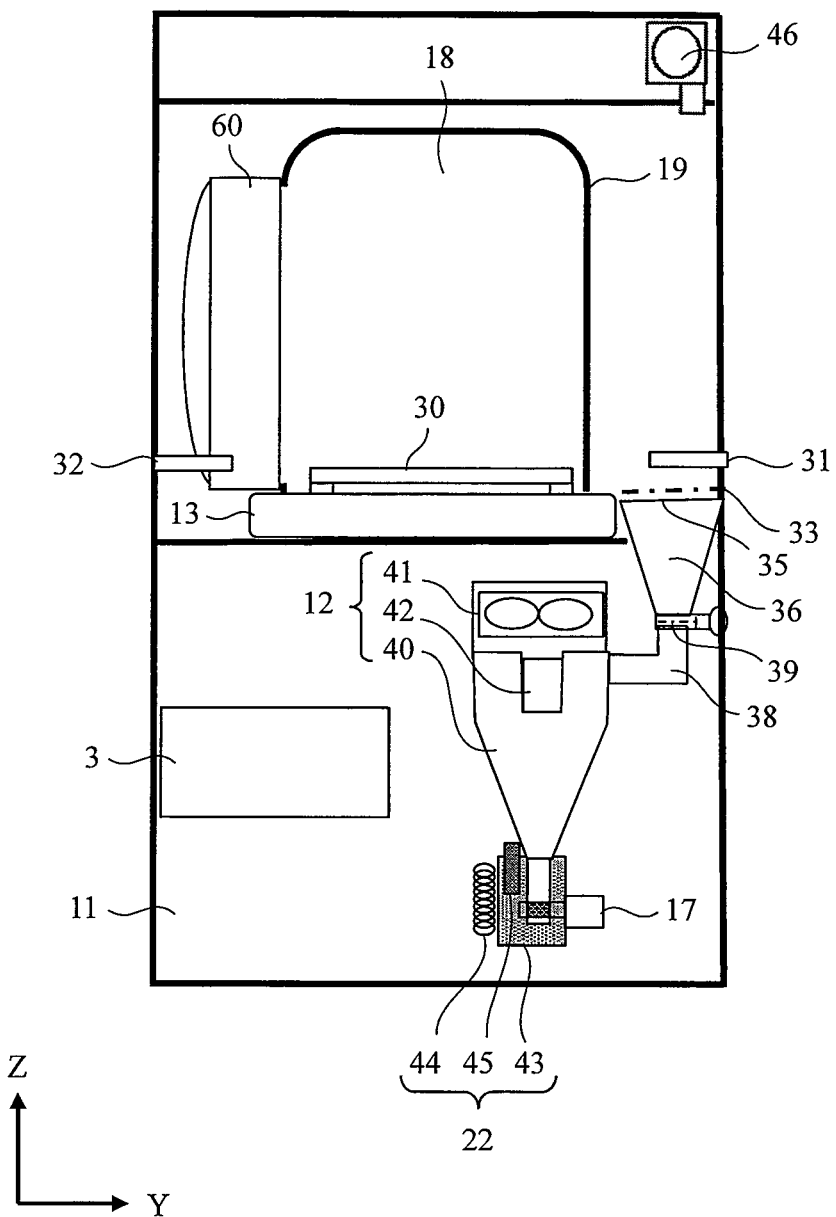
FIG. 20 is a schematic cross sectional view of the peeling/collection unit of an example of the attached matter inspection device according to the present invention.
Figure 21:
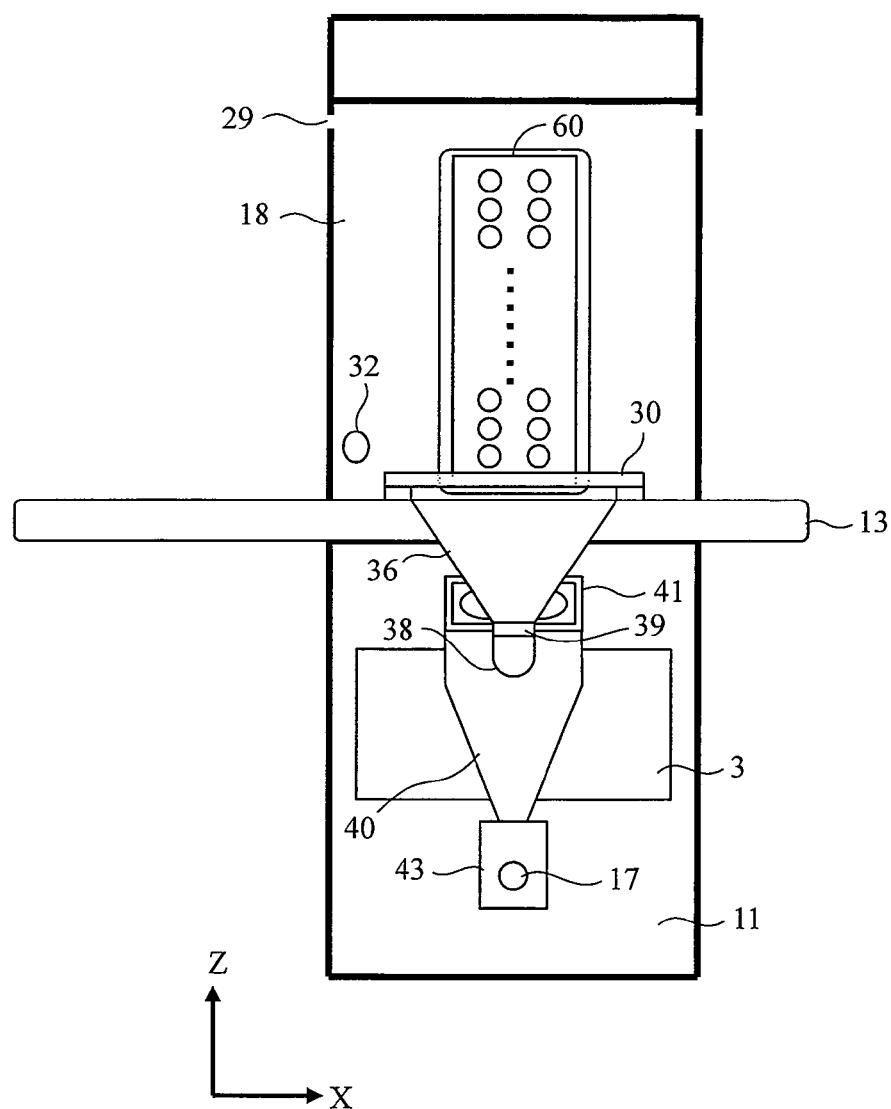
FIG. 21 is another schematic cross sectional view of the peeling/collection unit of an example of the attached matter inspection device according to the present invention.

The attached matter inspection device according to a third embodiment will be described. FIG. 20 is a schematic view corresponding to a cross section of the attached matter inspection device according to the present embodiment taken along line A-A' of FIG. 2, the cross section passing the inside of the sampling chamber entrance 29 of the sampling chamber 18 and being perpendicular to the inspection object delivery direction. In FIG. 20, illustration of the units of the attached matter inspection device 1 other than the heating unit 22, the operation panel 7, the power supply unit 6, and the compressed air generation unit 16 is omitted. FIG. 21 is a schematic view corresponding to a cross section of the device as viewed along the Y-axis direction of FIG. 2, showing a lateral view including a partial cross section of the sampling chamber 18. The cross section passes through the surface of the sampling chamber 18 to which the air nozzle unit 34 is attached, and parallel with the inspection object delivery direction. In FIG. 21, illustration of the units of the attached matter inspection device 1 other than the air nozzle unit 34, the inspection object recognition unit 14, and the delivery drive unit 13 is omitted.

In the third embodiment, as the air jet for peeling the fine particles from the inspection object, an air flow blown from a turbo fan 60 is used instead of the gas from the compressed air generation unit 16. In the attached matter inspection device 1 according to the present embodiment, the turbo fan 60 includes a total of 26 air jet blowing holes arranged in two columns along the Z-axis direction, as illustrated in FIG. 21. The wind speed of the air jet near the exit of the blowing holes may be approximately 80 m/s.

Figure 22:
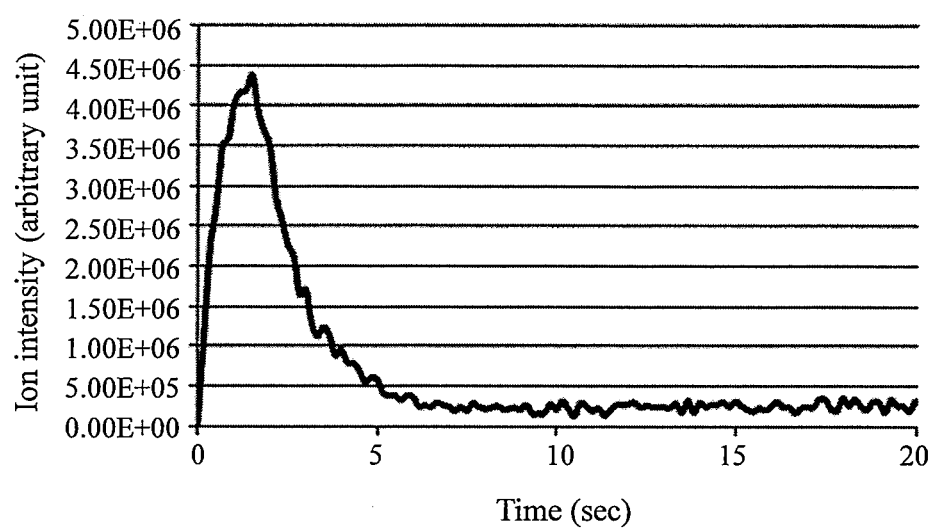
FIG. 22 is a chart illustrating a chronological change in the signal intensity of the mass-to-charge ratio of the trinitrotoluene explosive component detected from the inspection object to which trinitrotoluene explosive particles are attached.

FIG. 22 shows the result of an experiment for detecting explosive fine particles of trinitrotoluene from an inspection object using the configuration of the attached matter inspection device 1 illustrated in FIGS. 20 and 21. In FIG. 22, the horizontal axis shows time in seconds, and the vertical axis shows ion intensity in an arbitrary unit.

From the result of FIG. 22, it is seen that a signal indicating the trinitrotoluene explosive fine particles was detected from the inspection object with sufficient signal intensity. Specifically, it has been proven that the turbo fan 60 used in the present embodiment as peeling means provides an effective means of peeling the sample fine particles attached to the inspection object.

The use of the turbo fan 60 as the peeling means also eliminates the need for the compressed air generation unit 16. Because the turbo fan 60 uses electric power, the attached matter inspection device 1 may be provided with a number of air jet ejection holes without an increase in the size of the attached matter inspection device 1. Further, because air jets can be ejected from a number of blowing holes at the same time, the need for the control of selecting the air nozzles in accordance with the output from the inspection object recognition unit 14 is also eliminated. Thus, it is only necessary that the inspection object recognition unit 14 be provided with a set of a light projector and a light receiver for sensing the entry of the inspection object in the sampling chamber 18. Accordingly, a less expensive attached matter inspection device can be realized.

According to the present embodiment, there can be provided an attached matter inspection device that is smaller and that can perform the attached matter inspection with respect to a wider area of the inspection object.

Fourth Embodiment

The attached matter inspection devices described above use compressed gas or an air jet from the turbo fan 60 as a peeling means. The sample fine particles peeled from the inspection object by such means are transported to the collector 36 by being carried on the air flow of air jet described above. Thus, by providing the sampling chamber 18 with an internal guide wall 50 including a smooth curved surface for guiding the air flow produced in the sampling chamber 18 during peeling to the collector opening portion 35, the sample fine particles peeled from the inspection object can be transported to the collector 36 more efficiently.

Figure 23:
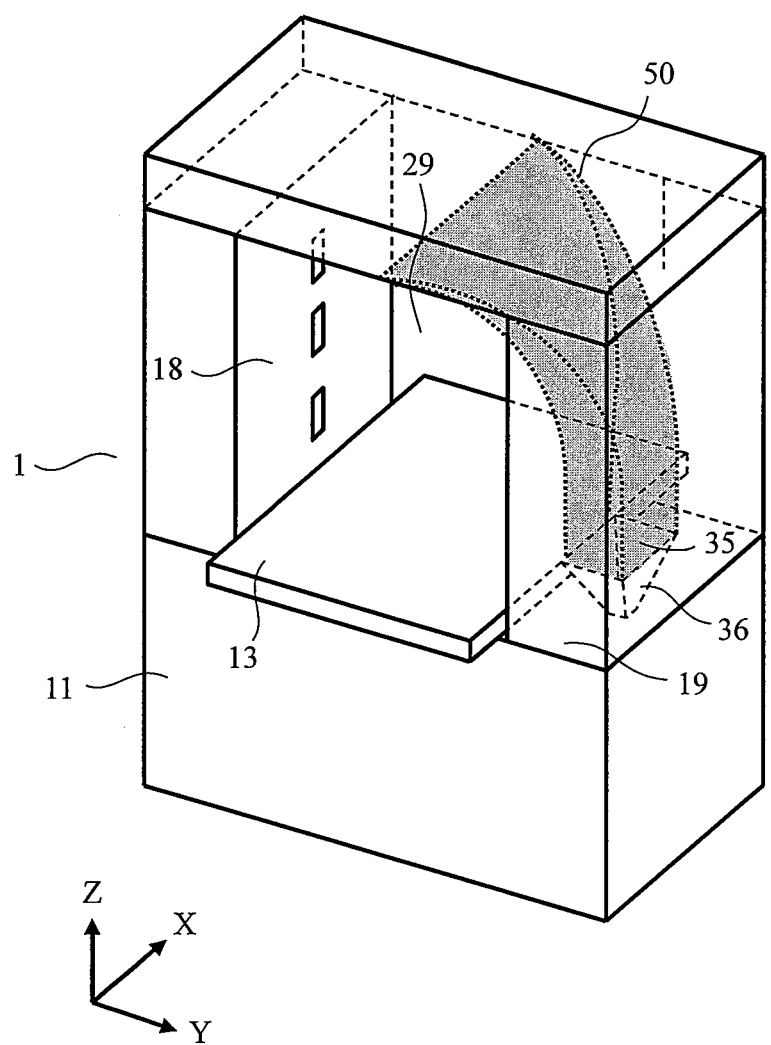
FIG. 23 is a perspective view of a guide wall in a sampling chamber.

FIG. 23 is a perspective view of the exterior of the attached matter inspection device 1 according to the fourth embodiment of the present invention.

The guide wall 50 includes a surface opposite the inspection object delivery surface which is opened in U shape in a cross section perpendicular to the Z-axis so as to take in the air jet flow, with both side surfaces being flanged to such an extent as not to interfere with the inspection object delivery space. The guide wall 50 is gradually inclined toward the center of the sampling chamber as the wall extends toward the top of the sampling chamber 18. The guide wall 50 as illustrated has the same length in the Y-axis direction of 20 cm as the collector, with the lower end of the guide wall 50 being coupled with the collector opening portion 35.

In the attached matter inspection device 1 according to the present embodiment, the flow of air jet used as the peeling means flows along the wall surface of the guide wall 50 and is guided to the collector 36. Thus, the sample fine particles similarly carried by the air flow can be guided to the collector 36 more efficiently with only a small amount of the particles being scattered in the sampling chamber 18. Because the guide wall 50 is provided, even when an explosive is detected, the portion on which the explosive fine particles remain attached is limited to the inner wall of the guide wall 50. Thus, in the attached matter inspection device 1 according to the present embodiment, an air flow can be caused on the inner wall of the guide wall 50 and therefore the inner wall of the guide wall 50 can be self-cleaned by simply performing air jet bombardment from the air nozzle unit 34 or the turbo fan 60 in the absence of the inspection object, without requiring a special air blower for self-cleaning.

In the attached matter inspection device 1 according to the present invention described above, the inspection object is of a size such that the inspection object can be carried on board an airplane. However, the range of the inspection object can be expanded by changing the shape of the sampling chamber entrance 29 of the sampling chamber 18. For example, at an airport, the sampling chamber entrance 29 may be increased in size so as to accommodate large-sized suit cases and the like consigned to an airline company. It is also possible to use the sampling chamber entrance 29 in combination with a human body scanner by matching the size of the sampling chamber entrance 29 to the size of the human body scanner, which may employ millimeter waves. By making the sampling chamber entrance 29 similar to the mail insertion opening of a mailbox, mail or tickets such as a boarding pass may be inspected.

Fifth Embodiment

The attached matter inspection device 1 described above may provide even higher inspection capability in combination with an X-ray transmission inspection device.

Figure 24:
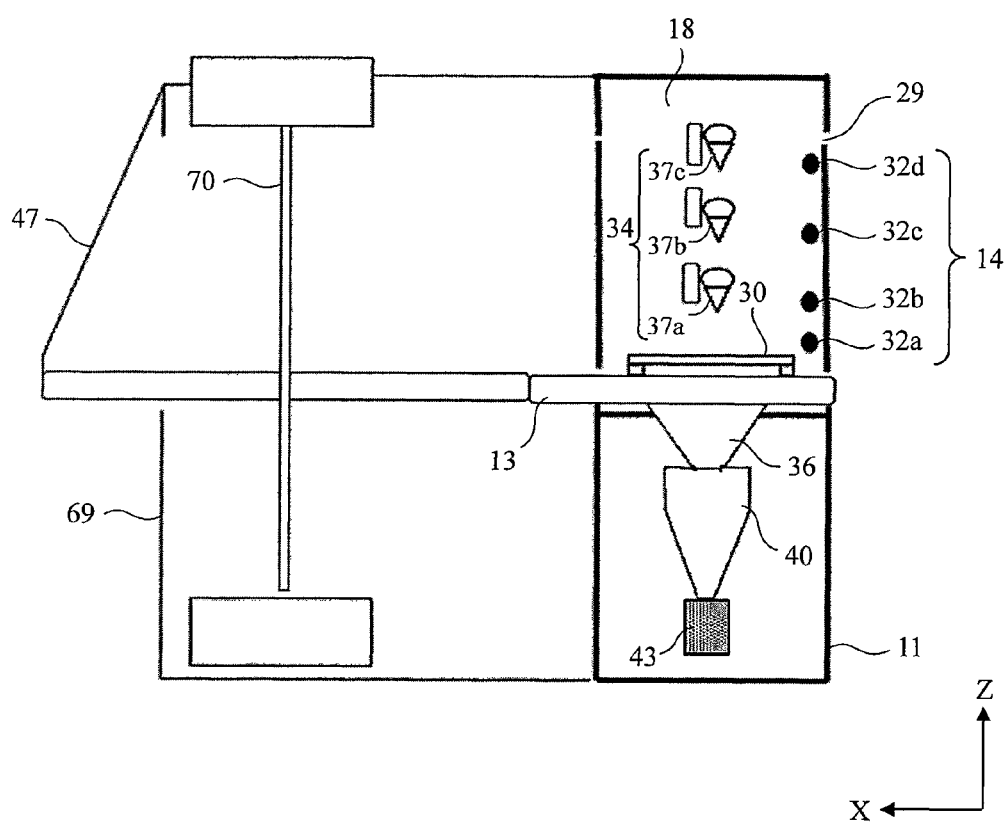
FIG. 24 is a schematic view of an integrated-type attached matter inspection device in which the attached matter inspection device according to the present invention and an X-ray transmission inspection device are connected in series.

FIG. 24 illustrates an embodiment in which the attached matter inspection device 1 according to the present invention is disposed in series with a conventional X-ray transmission inspection device 47. FIG. 24 is a lateral view of the embodiment corresponding to a partial cross section of FIG. 2 as viewed from the positive direction of the Y-axis. Numeral 70 designates an X-ray inspection region.

Figure 25:
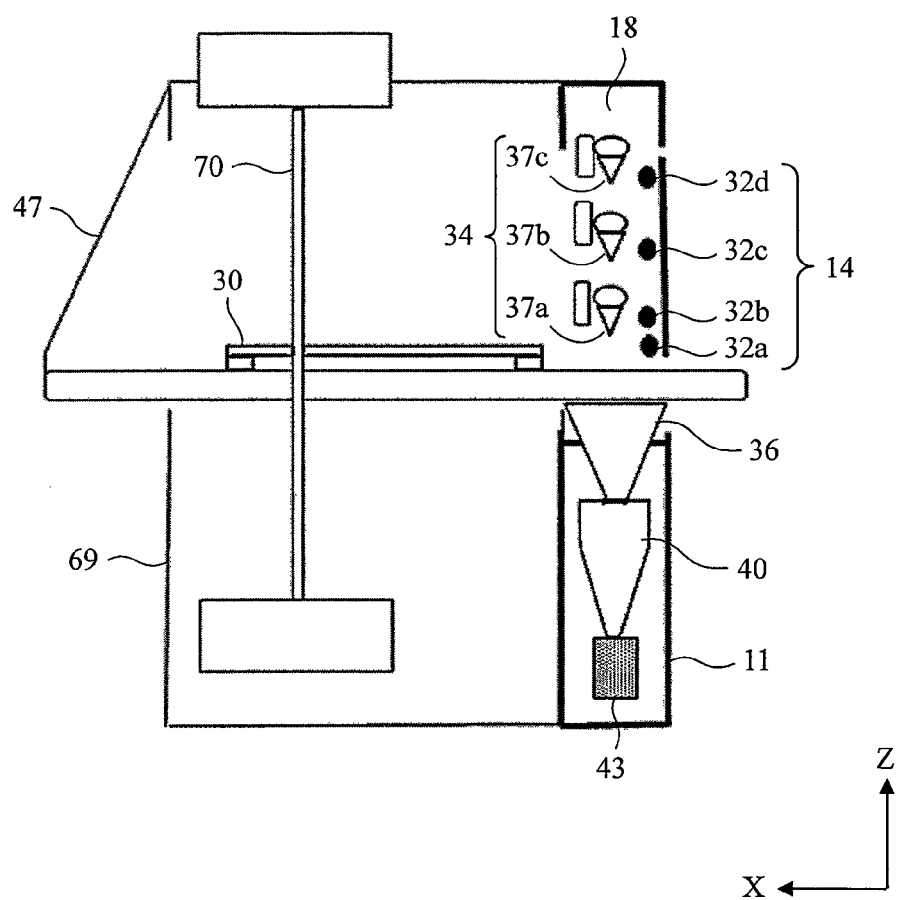
FIG. 25 is a schematic view of the integrated-type attached matter inspection device in which the attached matter inspection device according to the present invention is installed at an inspection object entrance of the X-ray transmission inspection device.

FIG. 25 illustrates an embodiment in which the attached matter inspection device 1 according to the present invention is installed at the entrance of the X-ray transmission inspection device 47. FIG. 25 is a lateral view of the embodiment corresponding to a partial cross section of FIG. 2 as viewed from the positive direction of the Y-axis.

In the embodiment of FIG. 25, the portions of the attached matter inspection unit 2 other than the heating unit 22, and various units other than the central control unit 3, the power supply unit 6, the inspection object recognition unit 14, the air nozzle unit 34, the collection unit 20, the separation unit 12, and the aspiration unit 21 are housed in an enclosure 69 of the X-ray transmission inspection device.

Figure 26:
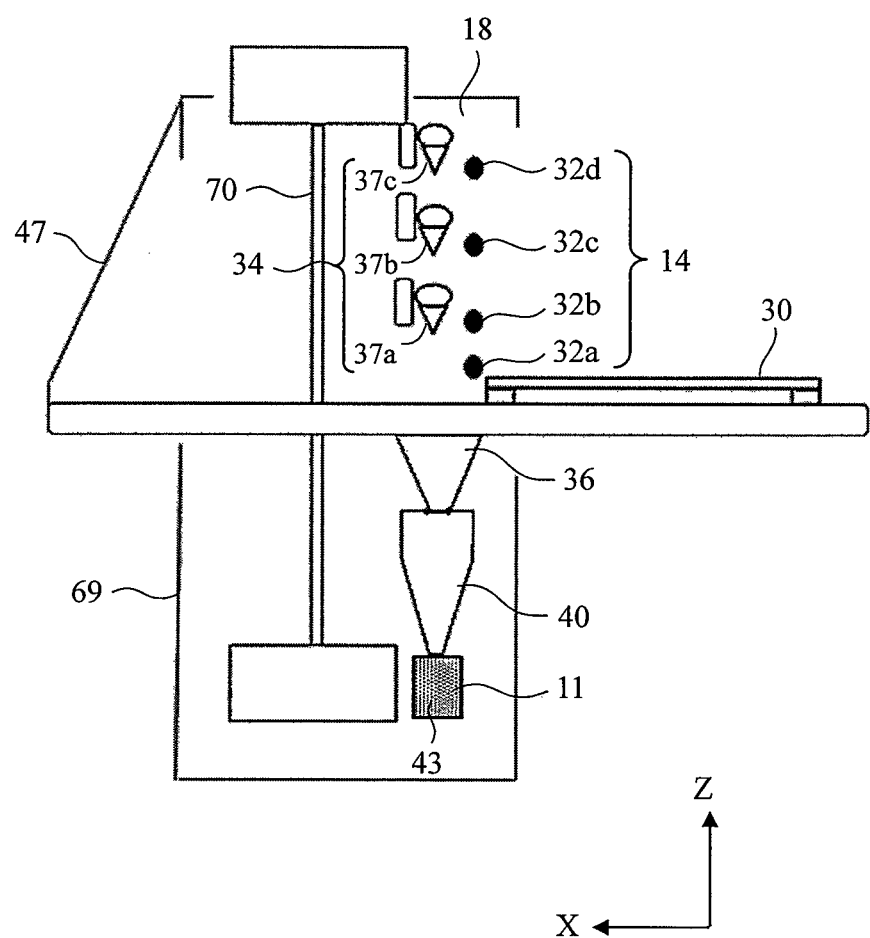
FIG. 26 is a schematic view of the integrated-type attached matter inspection device in which the attached matter inspection device according to the present invention is built inside the X-ray transmission inspection device.

FIG. 26 illustrates an embodiment in which the X-ray transmission inspection device 47 is integrally assembled with the attached matter inspection means according to the present invention. FIG. 26 is a lateral view corresponding to a partial cross section of FIG. 2 as viewed from the positive direction of the Y-axis.

In the X-ray transmission inspection device 47, the X-ray inspection region 70 for photography by X-ray bombardment is generally limited to a very limited location. Typically, the X-ray inspection region 70 is disposed at around the substantial center of the X-ray transmission inspection device 47. Thus, the attached matter inspection means according to the present embodiment can be assembled at a location other than the X-ray inspection region 70. In the present embodiment, the X-ray inspection region 70 is disposed behind the air nozzle unit 34.

According to the embodiments described with reference to FIG. 24, FIG. 25, and FIG. 26, inspection of the sample fine particles attached to the inspection object and X-ray inspection of the contents of the inspection object can be performed. Thus, the inspection reliability can be further increased. According to the embodiment illustrated in FIG. 26, a complex inspection device can be realized that can perform bulk inspection by X-ray and attached matter trace inspection simultaneously without increasing the occupied floor area beyond that of the existing X-ray transmission inspection device.

In the attached matter inspection device according to the present invention described above, the attendant may manually operate the air nozzles and cause the surface of the inspection object to be bombarded with an air jet, and still the same effect of peeling and collecting the sample fine particles from the inspection object and inspecting them can be obtained. In this case, the need for the inspection object recognition unit and the sampling chamber will be eliminated, making it possible to provide an attached matter inspection device which is less expensive, simpler, and smaller in size.

In the attached matter inspection device according to the present invention described above, the cyclone phenomenon is utilized as a means for separating the sample fine particles from the air flow. Alternatively, a well-known technology, such as an impactor, may be used as a separation means and still the same effect as that of the present invention can be obtained.

In the attached matter inspection device according to the present invention described above, a mass analysis means is used for the attached matter inspection unit 2. However, the present invention is not limited to the mass analysis means. For example, the present invention may be applied to a well-known chemical emission-type attached matter inspection device in which vapor of sample fine particles vaporized in an oven is separated using a gas chromatograph and reacted with a luminescent reagent to detect light emission and inspect the presence or absence of attached substance. The present invention may also be applied to a well-known ion mobility-type attached matter inspection device in which the vapor of the evaporated sample fine particles are ionized by a radioisotope in the ion source unit, and then introduced into a drift tube to detect the ion mobility and inspect the presence or absence of attached substance.

The present invention is not limited to the above-described embodiments and may include various modifications. The foregoing embodiments have been described for facilitating an understanding of the present invention, and are not necessarily limited to be provided with all of the described elements. Some of the elements of one embodiment may be substituted with elements of another embodiment, or an element of the other embodiment may be incorporated into an element of the one embodiment. With respect to some of the elements of each embodiment, addition, deletion, or substitution of another element may be made.

REFERENCE SIGNS LIST

1 Attached matter inspection device
2 Attached matter inspection unit
4 Inspection object delivery unit
5 Peeling/collection unit
11 Attached matter inspection device enclosure
17 Collection filter unit
18 Sampling chamber
19 Cover
28 Air nozzle
29 Sampling chamber entrance
30 Transport tray
31 Light projector
32 Light receiver
33 Mesh filter
34 Air nozzle unit
35 Collector opening portion
36 Collector
37 Air nozzle
38 Aspiration pipe
39 Coarse filter
40 Outer cylinder
41 Aspiration fan
42 Inner cylinder
43 Heat block
44 Heat source
45 Thermometer
46 Line air blower
47 X-ray transmission inspection device
48 Lower nozzle
49 Legged tray
50 Guide wall
60 Turbo fan
61 Air nozzle
62 Holder member
63 Rotating axis
64 Rotary joint
65 Bearing
66 Belt
67 Pulley
68 Rotary drive member
69 X-ray inspection device enclosure
70 X-ray inspection region

The invention claimed is:

1. An attached matter inspection device comprising:
a transport unit that transports an inspection object;
a sampling chamber defined by a pair of side walls and an upper wall enclosing a part of a transport route of the transport unit;
an air nozzle that sprays a gas onto the inspection object transported into the sampling chamber so as to peel sample fine particles attached to the inspection object;
a collector that aspirates air in the sampling chamber together with the sample fine particles; and
a separation unit that separates the sample fine particles from the aspirated air,
wherein the air nozzle is disposed on one of the side walls defining the sampling chamber, and the collector is disposed under the other side wall, and
the other side wall includes a groove portion extending in an upper-lower direction, the groove portion being connected to an opening portion of the collector.

2. The attached matter inspection device according to claim 1, wherein the collector has the opening portion disposed facing upward under the other side wall.

3. The attached matter inspection device according to claim 1, wherein the air nozzle sprays the gas onto the inspection object transported into the sampling chamber from a plurality of directions.

4. The attached matter inspection device according to claim 1, wherein the air nozzle is rotatably held about an axis parallel with a transport direction of the transport unit as a rotating axis.

5. The attached matter inspection device according to claim 1, wherein the sampling chamber includes an inner wall having a continuously curved shape for guiding the gas ejected from the air nozzle to the collector.

6. The attached matter inspection device according to claim 1, comprising a control unit that controls the air nozzle, wherein the control unit implements control for spraying the gas onto a front surface, a lateral surface, an upper surface, and a rear surface of the inspection object successively as the inspection object is moved by the transport unit.

7. The attached matter inspection device according to claim 1, wherein the air nozzle is also disposed on the side wall on the side on which the collector is disposed.

8. The attached matter inspection device according to claim 1, comprising:
a filter that collects the sample fine particles separated by the separation unit;
a heating unit that heats the filter;
an ion source that generates an ion of a sample gas generated from the sample fine particles by heating;
a mass analysis unit that obtains mass spectrum data of the sample gas by subjecting the ion to mass analysis;
a storage unit that stores standard mass spectrum data with regard to an explosive substance; and
a data processing unit,
wherein the data processing unit determines whether the sample fine particles attached to the inspection object are derived from the explosive substance by comparing the mass spectrum data of the sample gas and the standard mass spectrum data.

9. The attached matter inspection device according to claim 1, comprising a recognition unit that recognizes a size of the inspection object,
wherein the gas is ejected from the air nozzle that is allocated in advance in accordance with the size of the inspection object recognized by the recognition unit.

10. An attached matter inspection device comprising:
a transport unit that transports an inspection object;
a sampling chamber defined by a pair of side walls and an upper wall enclosing a part of a transport route of the transport unit;
a fan that peels sample fine particles attached to the inspection object by spraying air onto the inspection object transported into the sampling chamber;
a collector that aspirates air in the sampling chamber together with the sample fine particles; and
a separation unit that separates the sample fine particles from the aspirated air,
wherein the fan is disposed only on one of the side walls defining the sampling chamber, and the collector is disposed under the other side wall, and the sampling chamber includes an inner wall having a continuously curved shape for guiding the air blown from the fan to the collector.

11. The attached matter inspection device according to claim 10, wherein the collector has an opening portion disposed facing upward under the other side wall, and the inner wall of the sampling chamber includes a continuously curved shape for guiding the air blown from the fan to the opening portion of the collector.

12. An attached matter inspection device comprising:
   a transport unit that transports an inspection object;
   a sampling chamber defined by a pair of side walls and an upper wall enclosing a part of a transport route of the transport unit;
   an air nozzle that sprays a gas onto the inspection object transported into the sampling chamber so as to peel sample fine particles attached to the inspection object;
   a collector that aspirates air in the sampling chamber together with the sample fine particles;
   a separation unit that separates the sample fine particles from the aspirated air;
   a control unit that controls the air nozzle; and
   a recognition unit that recognizes a size of the inspection object,
   wherein the air nozzle is disposed on one of the side walls defining the sampling chamber, the collector is disposed under the other side wall and having an opening portion disposed facing upward under the other side wall, and
   the control unit implements control to cause the gas to be ejected from the air nozzle that is allocated in advance in accordance with the size of the inspection object recognized by the recognition unit, the gas being sprayed onto a front surface, a side surface, an upper surface, and a rear surface of the inspection object as the inspection object is moved by the transport unit.

* * * * *